(12) United States Patent
Mashiach

(10) Patent No.: US 8,588,941 B2
(45) Date of Patent: Nov. 19, 2013

(54) DEVICE AND METHOD FOR MODULATING NERVES USING PARALLEL ELECTRIC FIELDS

(71) Applicant: Adi Mashiach, Mont-St-Guibert (BE)

(72) Inventor: Adi Mashiach, Mont-St-Guibert (BE)

(73) Assignee: Nyxoah SA, Mont-St-Guibert (BE)

( * ) Notice: Subject to any disclaimer, the term of this patent is extended or adjusted under 35 U.S.C. 154(b) by 0 days.

(21) Appl. No.: 13/629,701

(22) Filed: Sep. 28, 2012

(65) Prior Publication Data

US 2013/0085558 A1    Apr. 4, 2013

Related U.S. Application Data

(60) Provisional application No. 61/541,651, filed on Sep. 30, 2011, provisional application No. 61/657,424, filed on Jun. 8, 2012.

(51) Int. Cl.
*A61N 1/05*    (2006.01)

(52) U.S. Cl.
USPC ............................ 607/134; 607/152; 607/156

(58) Field of Classification Search
USPC ......................................... 607/134, 152, 156
See application file for complete search history.

(56) References Cited

U.S. PATENT DOCUMENTS

| | | |
|---|---|---|
| 3,796,221 A | 3/1974 | Hagfors |
| 3,870,051 A | 3/1975 | Brindley |
| 4,765,983 A | 8/1988 | Takayanagi et al. |
| 4,830,008 A | 5/1989 | Meer |
| 4,837,049 A | 6/1989 | Byers et al. |
| 5,094,242 A | 3/1992 | Gleason et al. |
| 5,174,287 A | 12/1992 | Kallok et al. |
| 5,178,156 A | 1/1993 | Takishima et al. |
| 5,193,539 A | 3/1993 | Schulman et al. |
| 5,485,851 A | 1/1996 | Erickson |

(Continued)

FOREIGN PATENT DOCUMENTS

| | | |
|---|---|---|
| DE | 10 2009027997 | 1/2011 |
| WO | WO2007/098200 | 8/2007 |

(Continued)

OTHER PUBLICATIONS

Tran, W.H., "First Subject Evaluated with Simulated BION Treatment in Posterior Genioglossus to Prevent Obstructive Sleep Apnea." Sep. 2004. Proceedings of the 26th Annual International Conference of IEEE EMBS. pp. 4287-4289.*

(Continued)

*Primary Examiner* — Christopher D Koharski
*Assistant Examiner* — Michael Carey
(74) *Attorney, Agent, or Firm* — Finnegan, Henderson, Farabow, Garrett & Dunner LLP

(57) ABSTRACT

A device may include at least one pair of modulation electrodes configured for implantation in the vicinity of a nerve to be modulated such that the electrodes are spaced apart from one another along a longitudinal direction of the nerve to be modulated. The electrodes may be further configured to facilitate an electric field in response to an applied electric signal, the electric field including field lines extending in the longitudinal direction of the nerve to be modulated. The device may further include at least one circuit in electrical communication with the at least one pair of modulation electrodes and being configured to cause application of the electric signal applied at the at least one pair of modulation electrodes.

19 Claims, 16 Drawing Sheets

(56) References Cited

U.S. PATENT DOCUMENTS

| | | | |
|---|---|---|---|
| 5,540,733 A | 7/1996 | Testerman et al. | |
| 5,591,216 A | 1/1997 | Testerman et al. | |
| 5,697,076 A | 12/1997 | Troyk et al. | |
| 5,895,360 A | 4/1999 | Christopherson et al. | |
| 5,948,006 A | 9/1999 | Mann | |
| 6,024,702 A | 2/2000 | Iversen | |
| 6,026,818 A | 2/2000 | Blair et al. | |
| 6,038,480 A | 3/2000 | Hrdlicka et al. | |
| 6,051,017 A | 4/2000 | Loeb et al. | |
| 6,126,611 A | 10/2000 | Bourgeois et al. | |
| 6,163,725 A | 12/2000 | Peckham et al. | |
| 6,185,296 B1 | 2/2001 | Saitoh | |
| 6,210,326 B1 | 4/2001 | Ehwald | |
| 6,240,316 B1 | 5/2001 | Richmond et al. | |
| 6,275,737 B1 | 8/2001 | Mann | |
| 6,345,202 B2 | 2/2002 | Richmond et al. | |
| 6,572,543 B1 | 6/2003 | Christopherson et al. | |
| 6,587,725 B1 | 7/2003 | Durand et al. | |
| 6,587,728 B2 | 7/2003 | Fang et al. | |
| 6,625,494 B2 | 9/2003 | Fang et al. | |
| 6,636,767 B1 | 10/2003 | Knudson et al. | |
| 6,643,552 B2 | 11/2003 | Edell et al. | |
| 6,770,022 B2 | 8/2004 | Mechlenburg et al. | |
| 6,814,706 B2 | 11/2004 | Barton et al. | |
| 7,062,330 B1 | 6/2006 | Boveja et al. | |
| 7,155,278 B2 | 12/2006 | King et al. | |
| 7,272,443 B2 | 9/2007 | Min et al. | |
| 7,277,749 B2 | 10/2007 | Gordon et al. | |
| 7,295,132 B2 | 11/2007 | Steiner | |
| 7,367,935 B2 | 5/2008 | Mechlenburg et al. | |
| 7,371,220 B1 | 5/2008 | Koh et al. | |
| 7,447,551 B2 * | 11/2008 | Kuo et al. | 607/152 |
| 7,623,929 B1 | 11/2009 | Griffith | |
| 7,644,714 B2 | 1/2010 | Atkinson et al. | |
| 7,667,511 B2 | 2/2010 | Staszewski et al. | |
| 7,680,538 B2 | 3/2010 | Durand et al. | |
| 7,697,990 B2 | 4/2010 | Ujhazy et al. | |
| 7,709,961 B2 | 5/2010 | Greenberg et al. | |
| 7,725,195 B2 * | 5/2010 | Lima et al. | 607/60 |
| 7,729,772 B2 | 6/2010 | Williams et al. | |
| 7,729,781 B2 | 6/2010 | Swoyer et al. | |
| 7,733,218 B2 | 6/2010 | Drago et al. | |
| 7,756,583 B2 | 7/2010 | Demarais et al. | |
| 7,773,695 B2 | 8/2010 | Zhou et al. | |
| 7,809,442 B2 | 10/2010 | Bolea et al. | |
| 7,845,357 B2 | 12/2010 | Buscemi et al. | |
| 7,869,885 B2 | 1/2011 | Begnaud et al. | |
| 8,072,310 B1 | 12/2011 | Everhart | |
| 2001/0018547 A1 | 8/2001 | Mechienburg et al. | |
| 2002/0188333 A1 | 12/2002 | Nowick et al. | |
| 2003/0225403 A1 * | 12/2003 | Woloszko et al. | 606/41 |
| 2004/0049245 A1 | 3/2004 | Gass et al. | |
| 2004/0059392 A1 | 3/2004 | Parramon et al. | |
| 2004/0085792 A1 | 5/2004 | Lin et al. | |
| 2004/0102820 A1 | 5/2004 | Moune et al. | |
| 2004/0153127 A1 | 8/2004 | Gordon et al. | |
| 2004/0172089 A1 | 9/2004 | Whitehurst et al. | |
| 2004/0199212 A1 | 10/2004 | Fischell et al. | |
| 2005/0010265 A1 | 1/2005 | Baru Fassio et al. | |
| 2005/0043772 A1 | 2/2005 | Stahmann et al. | |
| 2005/0070971 A1 | 3/2005 | Fowler et al. | |
| 2005/0075694 A1 | 4/2005 | Schmeling et al. | |
| 2005/0075695 A1 | 4/2005 | Schommer | |
| 2005/0075700 A1 | 4/2005 | Schommer | |
| 2006/0062580 A1 | 3/2006 | Mahbobi | |
| 2006/0114104 A1 | 6/2006 | Scaramozzino | |
| 2006/0145878 A1 | 7/2006 | Lehrman et al. | |
| 2006/0180647 A1 | 8/2006 | Hansen | |
| 2006/0217779 A1 | 9/2006 | Ransbury et al. | |
| 2006/0224211 A1 | 10/2006 | Durand et al. | |
| 2006/0271110 A1 | 11/2006 | Vernon et al. | |
| 2007/0015022 A1 | 1/2007 | Chang et al. | |
| 2007/0073357 A1 | 3/2007 | Rooney et al. | |
| 2007/0112404 A1 | 5/2007 | Mann et al. | |
| 2007/0150022 A1 | 6/2007 | Ujhazy et al. | |
| 2007/0173893 A1 | 7/2007 | Pitts | |
| 2007/0185546 A1 | 8/2007 | Tseng et al. | |
| 2007/0221231 A1 | 9/2007 | Macken | |
| 2007/0222560 A1 | 9/2007 | Posamentier | |
| 2007/0233204 A1 | 10/2007 | Lima et al. | |
| 2007/0255379 A1 | 11/2007 | Williams et al. | |
| 2007/0265606 A1 | 11/2007 | DeBenedictis et al. | |
| 2007/0290859 A1 | 12/2007 | Held et al. | |
| 2008/0021506 A1 | 1/2008 | Grocela | |
| 2008/0027503 A1 | 1/2008 | Marrosu et al. | |
| 2008/0030363 A1 | 2/2008 | Rezvani et al. | |
| 2008/0041398 A1 | 2/2008 | Hegde et al. | |
| 2008/0081982 A1 | 4/2008 | Simon et al. | |
| 2008/0103407 A1 | 5/2008 | Bolea et al. | |
| 2008/0109046 A1 | 5/2008 | Lima et al. | |
| 2008/0109047 A1 | 5/2008 | Pless | |
| 2008/0119911 A1 | 5/2008 | Rosero | |
| 2008/0132962 A1 | 6/2008 | DiUbaldi et al. | |
| 2008/0140152 A1 | 6/2008 | Imran et al. | |
| 2008/0165058 A1 | 7/2008 | Ayachitula et al. | |
| 2008/0243014 A1 | 10/2008 | Moussavi et al. | |
| 2008/0300654 A1 | 12/2008 | Lambert et al. | |
| 2008/0319506 A1 | 12/2008 | Cauller | |
| 2009/0048647 A1 | 2/2009 | Tingey | |
| 2009/0062675 A1 | 3/2009 | Weigand et al. | |
| 2009/0069648 A1 | 3/2009 | Irazoqui et al. | |
| 2009/0078274 A1 | 3/2009 | Bhat et al. | |
| 2009/0132018 A1 | 5/2009 | DiUbaldi et al. | |
| 2009/0157150 A1 | 6/2009 | Cauller | |
| 2009/0173351 A1 | 7/2009 | Sahin et al. | |
| 2009/0281595 A1 | 11/2009 | King et al. | |
| 2010/0030298 A1 | 2/2010 | Martens et al. | |
| 2010/0087896 A1 | 4/2010 | McCreery | |
| 2010/0094379 A1 * | 4/2010 | Meadows et al. | 607/48 |
| 2010/0114190 A1 | 5/2010 | Bendett et al. | |
| 2010/0121413 A1 | 5/2010 | Willerton et al. | |
| 2010/0125304 A1 | 5/2010 | Faltys | |
| 2010/0131029 A1 | 5/2010 | Durand et al. | |
| 2010/0137948 A1 | 6/2010 | Aghassian et al. | |
| 2010/0139667 A1 | 6/2010 | Atkinson et al. | |
| 2010/0152553 A1 | 6/2010 | Ujhazy et al. | |
| 2010/0191136 A1 | 7/2010 | Wolford | |
| 2010/0196744 A1 | 8/2010 | Tucholski et al. | |
| 2010/0198305 A1 | 8/2010 | Farbarik | |
| 2010/0228313 A1 | 9/2010 | Starkebaum et al. | |
| 2010/0234924 A1 | 9/2010 | Willis | |
| 2010/0241195 A1 | 9/2010 | Meadows et al. | |
| 2010/0292527 A1 | 11/2010 | Schneider et al. | |
| 2010/0312320 A1 | 12/2010 | Faltys et al. | |
| 2010/0331634 A1 | 12/2010 | Muller et al. | |
| 2011/0065979 A1 | 3/2011 | Lehrman et al. | |
| 2011/0071591 A1 | 3/2011 | Bolea et al. | |
| 2011/0093036 A1 | 4/2011 | Mashiach | |
| 2011/0112601 A1 | 5/2011 | Meadows et al. | |
| 2011/0152965 A1 | 6/2011 | Mashiach et al. | |
| 2011/0152966 A1 | 6/2011 | Bolea et al. | |
| 2011/0172733 A1 | 7/2011 | Lima et al. | |
| 2011/0213438 A1 | 9/2011 | Lima et al. | |
| 2011/0230702 A1 | 9/2011 | Honour | |
| 2011/0264163 A1 | 10/2011 | Tracey et al. | |
| 2011/0301670 A1 | 12/2011 | Gross et al. | |
| 2012/0123498 A1 | 5/2012 | Gross | |

FOREIGN PATENT DOCUMENTS

| | | |
|---|---|---|
| WO | WO 2007/098202 | 8/2007 |
| WO | WO2008/048471 | 4/2008 |
| WO | WO 2011/077433 | 6/2011 |

OTHER PUBLICATIONS

Brindley, G.S., Transmission of electrical stimuli along many independent channels through a fairly small area of intact skin, Proceedings of the Physiological Society, Dec. 1964, pp. 44-46.

Tran W.H., First Subject Evaluated with Simulated BION Treatment in Posterior Genioglossus to Prevent Obstructive Sleep Apnea, Proceedings of the 26$^{th}$ Annual International Conference of IEEE EMBS, Sep. 2004, pp. 4287-4289.

(56) References Cited

OTHER PUBLICATIONS

Schwartz, Alan R., Therapeutic Stimulation of the Hypoglossal Nerve in Obstructive Sleep Apnea, Archives of Otolaryngology Head and Neck Surgery, vol. 127, Oct. 2001, pp. 1216-1223.

Eastwood, P.R., Treatment of Obstructive Sleep Apnea with Unilateral Hyopglossal Nerve Stimulation, American Journal of Respiratory Critical Care Medicine, vol. 181, May 2010, pp. 5393-5394.

Eisele, David W., Tongue neuromuscular and direct hypoglossal nerve stimulation for obstructive sleep apnea, Otolaryngologic Clinics of North America, Jun. 2003, pp. 501-510.

Robblee, L. S., Studies of the electrochemistry of stimulating electrodes, National Institutes of Health, Contract No. N01-NS-8-2313, Nov. 1991, pp. 6-8.

Levin, Morris, Nerve Blocks in the Treatment of Headaches, Neurotherapeutics; The Journal of the American Society for Experimental NeuroTherapeutics, Apr. 2010, pp. 197-203.

Lundy, Larry, Ear, Nose, and Throat Journal, Cochlear Implant Fixation Using Resortable Mesh, Jul. 1, 2011, 4 pages.

Youbok Lee, "Antenna Circuit Design for RFID Applications," Microchip Technology Inc., Dec. 5, 2002. pp. 1-50.

Upson, James; King, Frederick; Roberts, Lamar; A constant amplitude transistorized unit for remote brain stimulation, Electroencephalography and Clinical Neurophysiology, Jun. 11, 1962.

Brindley, G.S., An implant to empty the bladder or close the urethra, Journal of Neurology, Neurosurgery, and Psychiatry, 1977.

Kaplan, Hilton; Loeb, Gerald; Design and Fabrication of an Injection Tool for Neuromuscular Microstimulators, Annals of Biomedical Engineering, vol. 37, No. 9., Jun. 24, 2009.

Troyk, Philip; Schwan, Martin; Closed-Loop Class E Transcutaneous Power and Data Link for MicroImplants. IEEE Transactions on Biomedical Engineering, vol. 39, No. 6, Jun. 1992.

Mithun, Joe; Rajkumar, Vikram; Shanmugapriya; Apnea Detecting Sensors; Sathyabama Deemed University, 2006.

Babak, Ziaie; Nardin, Mark; Coghlan, Anthony; Najafi, Khalil, A Single-Channel Implantable Microstimulator for Functional Neuromuscular Stimulation, IEEE Transactions on Biomedical Engineering, vol. 44, No. 10, Oct. 1997.

Robin, S; Sawan, M.; Harvey, J.F.; Abdel-Gawad, M.; Abdel-Baky, T.M.; Elhili, M.M., A New Implantable Microstimulator Dedicated to Selective Stimulation of the Bladder, 19th International Conference, IEEE/EMBS Oct. 30-Nov. 2, 1997.

Troyk, P.R.; Donaldson N. de N.; Implantable FES Stimulation Systems: What is Needed, 2001 Neuromodulation Society, Neuromodulation, vol. 4, No. 4, 2001.

Loeb, Gerald; Richmond, Frances; Moore, W. Henry; Peck, Raymond, 1st Annual International IEEE-EMBS Special Topic Conference on Microtechnologies in Medicine & Biology, Oct. 2000.

Harrison, Reid, Designing Efficient Inductive Power Links for Implantable Devices, University of Utah, 2007.

Mohtashami, Saba, Electrochemical Properties of Flexible Electrodes for Implanted Neuromuscular Excitation Applications, McMaster University, Oct. 1, 2011.

Baker, Michael; Sarpeshkar, Rahul, Feedback Analysis and DEsign of Rf Power Links for Low-Power Bionic Systems, IEEE Transactions on Biomedical Circuits and Systems, vol. 1, No. 1, Mar. 2007.

Zierhofer, Clemens, HOchmair, Erwin, High-Efficiency Coupling-Insensitive Transcutaneous Power and Data Transmission Via an Inductive Link, IEEE Transactions on Biomedical Engineering, vol. 37, No. 3, Jul. 1990.

Tran, W.H., Loeb, G.E., Richmond, F.J.R.; Ahmed, R.; Clark, G.T.; Haberman, P.B., First Subject Evaluated with Simulated BION Treatment in Posterior Genioglossus to Prevent Obstructive Sleep Apnea, Proceedings of the 26th Annual International Conference of the IEEE EMBS, San Francisco, CA, USA, Sep. 2004.

Jow, Uei-Ming; Ghovanloo, Maysam, Design and Optimization of Printed Spiral Coils for Efficient Transcutaneous Inductive Power Transmission, IEEE Transactions on Biomedical Circuits and Systems, vol. 1, No. 3, Sep. 2007.

Steiglitz, Thomas, Polymer-based Substrates and Flexible Hybrid Assembly Techniques for Implantable Active Microdevices, Business Briefing: Medical Device Manufacturing & Technology, 2002.

Jarvis, Jonathan; Salmons, Stanley, The Application and Technology of Implantable Neuromuscular StimulatorsL an introduction and overview, Medical Engineering and Physics 23, 2001.

Manola, Ljubomir; Holsheimer, Jan; Veltink, Peter; Bradley, Kerry; Peterson, David, Theoretical Investigation Into Longitudinal Cathodal Field Steering in Spinal Cord Stimulation, Neurmodulation: Technology at the Neural Interface, vol. 10, No. 2, 2007.

Joho, Dominik, Plagemann, Christian, Burgard, Wolfram, Modeling RFID Signal Strength and Tag Detection for Localization and Mapping, Proceedings of the IEEE International Conference on Robotics and Automation, Kobe Japan, May 2009.

Werber, D.; Schwentner, A.; Biebl, E.M., Investigation of RF Transmission Properties of Human Tissues, Advances in Radio Science, vol. 4, 2006.

Cameron, Tracy; Loeb, Gerald; Peck, Raymond; Schulman, Joseph; Strojnik, Primoz; Troyk, Philip, Micromodular Implants to Provide Electrical Stimulation of Paralyzed Muscles and Limbs, IEEE Transactions on Biomedical Engineering, vol. 44, No. 9, Sep. 1997.

Mokwa, Wilfried; Schnakenberg, Uwe, Micro-Transponder Systems for Medical, IEEE Transactions on Instrumentation and Measurement, vol. 50, No. 6, Dec. 2001.

Grill, Warren; Veraart, Claude; Mortimer, Thomas, Selective Activation of Peripheral Nerve Fascicles: Use of Field Steering Currents, Annual International Conference of the IEEE Engineering in Medicine and Biology Society, vol. 13, No. 2, 1991.

Loeb, G.E.; Zamin, C.J.; Schulman, J.H.; Troyk, P.R., Injectable Microstimulator for Functional Electrical Stimulation, Med. and Biol. Eng. & Comput. 1991.

Young, Darrin, Wireless Powering and Data Telemetry for Biomedical Implants, 31st Annual International Conference of the IEEE EMBS, Minnesota, USA, Sep. 2009.

Han, J.H.; Lim, H.G.; Kim, J.M.; Lee, C.W.; Park, I.Y.; Cho, J.H., Inductively-Coupled Control Unit for Fully Implantable Middle Ear Hearing Devices, Proceedings of the 2005 IEEE Engineering in Medicine and Biology 27th Annual Conference, China, Sep. 2005.

Oliven, A; Kaufman, E.; Kaynan, R.; Golboda, T.; Oliven, R.; Geitini, L.; Odeh, M.; Tov, N.; Schwartz, A.R.; Kimel, E., Effects of Cross-Sectional Area, Compliance and External Pressure on Pharyngeal Collapsibility in Patients With Obstructive Sleep Apnea, A68 Upper Airway and Repiratory Physiology, 2010.

Yoo, Paul B.; Durand, Dominique, Effects of Selective Hypoglossal Nerve Stimulation on Canine Upper Airway Mechanics, Journal of Applied Physiology, 2005.

Huang, Jingtao; Sahin, Mesut; Durand, Dominique, Dilation of the oropharynx via selective stimulation of the hypoglossal nerve, Journal of Neural Engineering, 2005.

Oliven, A; Tov, N.; Geitini, L.; Steinfeld, U.; Oliven, R.; Schwartz, A.R.; Odeh, M., Effect of Genioglossus Contraction on Pharyngeal Lumen and Airflow in Sleep Apnoea Patients, European Respiratory Journal, 2007.

Davis, Ross; Cosendai, Gregoire; Arcos, Isabel; Kushner, Douglas; Mishler, Delta; Decker, Christopher; Ripley, Anne-Marie; Maceri, Dennis; Sanderson, Donna; Zilberman, Yitzhak; Schulman, Joseph, Development of the BION Microstimulator for Treatment in Obstructive Sleep Apnea, Alfred Mann Foundation.

Eastwood, P.R.; Barnes, M.; McEvoy, R.D; Wheatley, J; Walsh, J.H.; O'Donoghue, F.J.; Catcheside, P.; Tyler, L.; Maddison, K.J.; Rochford, P.D.; Antic, N.; Worsnop C.; Churchward, T.; Eckert, D.J.; Campbell, M.C., Hee, G.; Palme, C.E., Robinson, S.H.; Kezirian, E.; Goding, G.; Jordan, A.S.; Smith, P.L.; Schwartz, A.R.; Malhotra, A.; Hillman, D.R., Feasibility of Hypoglossal Nerve Stimulation Therapy to Treat Obstructive Sleep Apnea, Am. J. Respir Crit Care Med, 2010.

Randerath, Winfried, Electrical Stimulation of the Upper Airways Muscles, Institute for Pheumology at the University Witten/Herdecke, 2006.

Schwartz, Alan; Eisele, David; Han, Anil; Testerman, Roy; Erickson, Donald; Smith, Philip, Electrical Stimulation of the Lingual Musculature in Obstructive Sleep Apnea, Johns Hopkins Asthma and Allergy Center, Feb. 1996.

(56) References Cited

OTHER PUBLICATIONS

Kezirian, Eric J.; Boudewyns, An; Eisele, David; Schwartz, Alan; Philip, Smith; Van de Heyning, Paul; De Backer, Wilfried, Electrical Stimulation of the Hypoglossal Nerve in the Treatment of Obstructive Sleep Apnea, Sleep Medicine Reviews, 2009.
Isono, S.; Tanaka, A.; Nishino, T., Effects of Tongue Electrical Stimulation on Pharyngeal Mechanics in Anaesthetized Patients with Obstructive Sleep Apnoea, Eur Respir J, 1999.
Fregosi, Ralph, Influence of Tongue Muscle Contraction and Dynamic Airway Pressure on Velopharyngeal Volume in the Rat, J. Appl. Physiol, Dec. 2007.
Van de Heyning, Paul; Badr, M. Safwan; Baskin, Jonathan Z.; Bornemann, Michael Cramer; De Backer, Wilfried A.; Dotan, Yaniv; Hohenhorst, Winfried; Knaack, Lennart; Lin, Ho-Sheng, Maurer, Joachim T.; Netzer, Aviram; Odland, Rick M.; Oliven, Arie; Strohl, Kingman P.; Vanderveken, Olivier M.; Verbraecken, Johan; Woodson, B. Tucker, Implanted Upper Airway Stimulation Device for Obstructive Sleep Apnea, The Laryngoscope, Jul. 2012.
Oliven, Ron; Tov, Naveh; Odeh, Majed; Gaitini, Luis; Steinfeld, Uri; Schwartz, Alan; Oliven, Arie, Interacting Effects of Genioglossus Stimulation and Mandibular Advancements in Sleep Apnea, J. Appl. Physiol, 2009.
Peng, Chih-Wei; Chen, Jia-Jin Jason; Lin, Chou-Ching K.; Poon, Paul Wai-Fung; Liang, Chih-Kuo; Lin, Kang-Ping, High Frequency Block of Selected Axons Using an Implantable Microstimulator, 2004.
Burnett, Theresa; Mann, Eric; Cornell, Sonia; Ludlow, Christy, Laryngeal Elevation Achieved by Neuromuscular Stimulation at Rest, J. Appl. Physiol. 94, 2003.
Hu, Linggang; Xu, Xiaomei; Gong, Yongsheng; Fan, Xiaofang; Wang, Liangxing; Zhang, Jianhua, Percutaneous Biphasic Electrical Stimulation for Treatment of Obstructive Sleep Apnea Syndrom, IEEE Transactions on Biomedical Engineering, vol. 55, No. 1, Jan. 2008.
Dotan, Y.; Goliboda, T.; Netzer, A.; Geitini, L.; Oliven, A., Parameters Affecting the Mechanical Effect of Electrical Stimulation (ES) of the Tongue Muscles in Patients with Obstructive Sleep Apnea (OSA), Am. J. Respir. Crit Care Med, 2010.
Yoo, Paul Byong-Suk, Selective Stimulation and Recording of the Canine Hypoglossal Nerve for the Treatment of Obstructive Sleep Apnea, Case Western Reserve University, May 2004.
Oliven, Arie, Treating Obstructive Sleep Apnea With Hypoglossal Nerve Stimulation, Curr. Opin. Pulm. Med. 2011.
Goding, George; Eisele, David; Testerman, Roy; Smith, Philip; Roertgen, Karen; Schwartz, Alan, Relief of Upper Airway Obstruction With Hypoglossal Nerve Stimulation in the Canine, Laryngoscope, 1998.
Oliven, Arie; Schnall, Robert; Pillar, Giora; Gavriely, Noam; Oden, Majed, Sublingual Electrical Stimulation of the Tongue During Wakefulness and Sleep, Respiration Physiology, 127, 2001.
Mwenge, Gimbada; Rombaux, Phillippe; Dury, Myriam; Lengele, Benoit; Rodenstein, Daniel, Targeted Hypoglossal Neurostimulation for Obstructive Sleep Apnea. A 1 year pillot study, ERJ Express, May 17, 2012.
Mann, Eric; Burnett, Theresa; Cornell, Sonia; Ludlow, Christy, The Effect of Neuromuscular Stimulation of the Genioglossus on the Hypopharyngeal Airway, The Laryngoscope, 2002.
Oliven, Arie; O'Hearn, Daniel; Boudewyns, An; Odeh, Majed; De Backer, Wilfried; van de Heyning, Paul; Smith, Philip; Eisele, David; Allan, Larry; Schneider, Hartmut; Testerman, Roy; Schwartz, Alan, Upper Airway Response to Electrical Stimulation of the Genioglossue in Obstructive Sleep Apnea, J. Appl. Physiol. vol. 95, 2003.
Guillemenivalt, Christian; Powell, Nelson; Bowman, Bruce; Stoohs, Riccardo, The Effect of Electrical Stimulation on Obstructive Sleep Apnea Syndrome, Chest, Jan. 1995.
Eastwood, Peter; Barnes, Maree; Walsh, Jennifer; Maddison, Kathleen; Hee, Geoffrey; Schwartz, Alan; Smith, Philip; Malhotra, Atul; McEvoy, Douglas; Wheatley, John; O'Donoghue, Fergal; Rochford, Peter; Churchward, Tom; Campbell, Matthew; Palme, Carsten; Robinson, Sam; Goding, George; Eckert, Danny; Jordan, Amy; Catcheside, Peter; Tyler, Louise; Antic, Nick; Worsnop, Christopher; Kezirian, Eric; Hillman, David, Treating Obstructive Sleep Apnea with Hypoglossal Nerve Stimulation, Sleep vol. 34, No. 11, 2011.
Schwartz, Alan; Bennet, Marc; Smith, Philip; De Backer, Wilfried; Hedner, Jan; Boudewyns, An; Van de Heyning, Paul; Ejnell, Hasse; Hochban, Walter; Knaack, Lennart; Podszus, Thomas; Penzel, Thomas; Peter, J. Hermann; Goding, George; Erickson, Donald; Testerman, Roy; Ottenhoff, Frans; Eisele, David, Therapeutic Electrical Stimulation of the Hypoglossal Nerve in Obstructive Sleep Apnea, Arch Otolaryngol Head Neck Surg, vol. 127, Oct. 2001.
Randerath, Winfried, Galetke, Wolfgang; Domanski, Uinke; Weitkunat, Rolf; Ruhle, Karl-Heinz, Tongue-Muscle Training by Intraoral Electrical Neurostimulation in Patients with Obstructive Sleep Apnea, Sleep, vol. 27, No. 2, 2004.
Eastwood, P.R.; Walsh, J.H.; Maddison, K.J.; Baker, V.A.; Tesfayesus, W.; Hillman, D.R., Treatment of Obstructive Sleep Apnea With Unilateral Hypoglossal Nerve Stimulation, Am J Respir Crit Care Med 181, 2010.
Loeb, Gerald; Richmond, Frances; Baker, Lucinda, The BION devices: injectable interfaces with peripheral nerves and muscles, Neurosurgery Focus 20, 2006.
Co-Pending U.S. Appl. No. 13/629,686, filed Sep. 28, 2012.
Co-Pending U.S. Appl. No. 13/629,694, filed Sep. 28, 2012.
Co-Pending U.S. Appl. No. 13/630,392, filed Sep. 28, 2012.
Co-Pending U.S. Appl. No. 13/629,762, filed Sep. 28, 2012.
Co-Pending U.S. Appl. No. 13/629,793, filed Sep. 28, 2012.
Co-Pending U.S. Appl. No. 13/629,819, filed Sep. 28, 2012.
Co-Pending U.S. Appl. No. 13/629,690, filed Sep. 28, 2012.
Co-Pending U.S. Appl. No. 13/629,748, filed Sep. 28, 2012.
Co-Pending U.S. Appl. No. 13/629,757, filed Sep. 28, 2012.
Co-Pending U.S. Appl. No. 13/629,712, filed Sep. 28, 2012.
Co-Pending U.S. Appl. No. 13/629,730, filed Sep. 28, 2012.
Co-Pending U.S. Appl. No. 13/629,725, filed Sep. 28, 2012.
Co-Pending U.S. Appl. No. 13/629,741, filed Sep. 28, 2012.
Co-Pending U.S. Appl. No. 13/629,721, filed Sep. 28, 2012.
International Searching Authority, International Search Report and Written Opinion of the International Searching Authority, International Application No. PCT/IB12/02442, mailed May 28, 2013.

* cited by examiner

DEVICE AND METHOD FOR MODULATING NERVES USING PARALLEL ELECTRIC FIELDS

RELATED APPLICATIONS

This application claims the benefit of priority under 35 U.S.C. §119(e) to U.S. Provisional Application No. 61/541,651, filed Sep. 30, 2011, and also to U.S. Provisional Application No. 61/657,424, filed Jun. 8, 2012, all of which are incorporated herein by reference in their entirety.

TECHNICAL FIELD

Embodiments of the present disclosure generally relate to devices and methods for modulating a nerve. More particularly, embodiments of the present disclosure relate to devices and methods for modulating a nerve through the delivery of energy via an implantable electrical modulator.

BACKGROUND

Neural modulation presents the opportunity to treat many physiological conditions and disorders by interacting with the body's own natural neural processes. Neural modulation includes inhibition (e.g. blockage), stimulation, modification, regulation, or therapeutic alteration of activity, electrical or chemical, in the central, peripheral, or autonomic nervous system. By modulating the activity of the nervous system, for example through the stimulation of nerves or the blockage of nerve signals, several different goals may be achieved. Motor neurons may be stimulated at appropriate times to cause muscle contractions. Sensory neurons may be blocked, for instance to relieve pain, or stimulated, for instance to provide a signal to a subject. In other examples, modulation of the autonomic nervous system may be used to adjust various involuntary physiological parameters, such as heart rate and blood pressure. Neural modulation may provide the opportunity to treat several diseases or physiological conditions, a few examples of which are described in detail below.

Among the conditions to which neural modulation may be applied is obstructive sleep apnea (OSA). OSA is a respiratory disorder characterized by recurrent episodes of partial or complete obstruction of the upper airway during sleep. During the sleep of a person without OSA, the pharyngeal muscles relax during sleep and gradually collapse, narrowing the airway. The airway narrowing limits the effectiveness of the sleeper's breathing, causing a rise in $CO_2$ levels in the blood. The increase in $CO_2$ results in the pharyngeal muscles contracting to open the airway to restore proper breathing. The largest of the pharyngeal muscles responsible for upper airway dilation is the genioglossus muscle, which is one of several different muscles in the tongue. The genioglossus muscle is responsible for forward tongue movement and the stiffening of the anterior pharyngeal wall. In patients with OSA, the neuromuscular activity of the genioglossus muscle is decreased compared to normal individuals, accounting for insufficient response and contraction to open the airway as compared to a normal individual. This lack of response contributes to a partial or total airway obstruction, which significantly limits the effectiveness of the sleeper's breathing. In OSA patients, there are often several airway obstruction events during the night. Because of the obstruction, there is a gradual decrease of oxygen levels in the blood (hypoxemia). Hypoxemia leads to night time arousals, which may be registered by EEG, showing that the brain awakes from any stage of sleep to a short arousal. During the arousal, there is a conscious breath or gasp, which resolves the airway obstruction. An increase in sympathetic tone activity rate through the release of hormones such as epinephrine and noradrenaline also often occurs as a response to hypoxemia. As a result of the increase in sympathetic tone, the heart enlarges in an attempt to pump more blood and increase the blood pressure and heart rate, further arousing the patient. After the resolution of the apnea event, as the patient returns to sleep, the airway collapses again, leading to further arousals.

These repeated arousals, combined with repeated hypoxemia, leaves the patient sleep deprived, which leads to daytime somnolence and worsens cognitive function. This cycle can repeat itself up to hundreds of times per night in severe patients. Thus, the repeated fluctuations in and sympathetic tone and episodes of elevated blood pressure during the night evolve to high blood pressure through the entire day. Subsequently, high blood pressure and increased heart rate may cause other diseases.

Efforts for treating OSA include Continuous Positive Airway Pressure (CPAP) treatment, which requires the patient to wear a mask through which air is blown into the nostrils to keep the airway open. Other treatment options include the implantation of rigid inserts in the soft palate to provide structural support, tracheotomies, or tissue ablation.

Another condition to which neural modulation may be applied is the occurrence of migraine headaches. Pain sensation in the head is transmitted to the brain via the occipital nerve, specifically the greater occipital nerve, and the trigeminal nerve. When a subject experiences head pain, such as during a migraine headache, the inhibition of these nerves may serve to decrease or eliminate the sensation of pain.

Neural modulation may also be applied to hypertension. Blood pressure in the body is controlled via multiple feedback mechanisms. For example, baroreceptors in the carotid body in the carotid artery are sensitive to blood pressure changes within the carotid artery. The baroreceptors generate signals that are conducted to the brain via the glossopharyngeal nerve when blood pressure rises, signaling the brain to activate the body's regulation system to lower blood pressure, e.g. through changes to heart rate, and vasodilation/vasoconstriction. Conversely, parasympathetic nerve fibers on and around the renal arteries generate signals that are carried to the kidneys to initiate actions, such as salt retention and the release of angiotensin, which raise blood pressure. Modulating these nerves may provide the ability to exert some external control over blood pressure.

The foregoing are just a few examples of conditions to which neuromodulation may be of benefit, however embodiments of the invention described hereafter are not necessarily limited to treating only the above-described conditions.

SUMMARY

A device may include at least one pair of modulation electrodes configured for implantation in the vicinity of a nerve to be modulated such that the electrodes are spaced apart from one another along a longitudinal direction of the nerve to be modulated. The electrodes may be further configured to facilitate an electric field in response to an applied electric signal, the electric field including field lines extending in the longitudinal direction of the nerve to be modulated. The device may further include at least one circuit in electrical communication with the at least one pair of modulation electrodes and being configured to cause application of the electric signal applied at the at least one pair of modulation electrodes. A method of modulating a nerve may include receiving an alternating current (AC) signal at a device configured to be implanted into a body of a subject and generating a voltage signal in response to the AC signal. The method may further include applying the voltage signal to at least one pair of modulation electrodes configured for implantation in the vicinity of the nerve such that the electrodes are spaced apart from one another along a longitudinal direction of the nerve; generating an electrical field in response to the voltage signal applied to the at least one pair of modulation electrodes, the electric field including field lines extending in a longitudinal direction of the nerve; and modulating the nerve.

Additional features of the disclosure will be set forth in part in the description that follows, and in part will be obvious from the description, or may be learned by practice of the disclosed embodiments.

It is to be understood that both the foregoing general description and the following detailed description are exemplary and explanatory only, and are not restrictive of the invention, as claimed.

BRIEF DESCRIPTION OF THE DRAWINGS

The accompanying drawings, which are incorporated in and constitute a part of this specification, illustrate several embodiments of the disclosure and, together with the description, serve to explain the principles of the embodiments disclosed herein.

DESCRIPTION OF EXEMPLARY EMBODIMENTS

Reference will now be made in detail to exemplary embodiments of the present disclosure, examples of which are illustrated in the accompanying drawings. Wherever possible, the same reference numbers will be used throughout the drawings to refer to the same or like parts.

Embodiments of the present disclosure relate generally to a device for modulating a nerve through the delivery of energy. Nerve modulation, or neural modulation, includes inhibition (e.g. blockage), stimulation, modification, regulation, or therapeutic alteration of activity, electrical or chemical, in the central, peripheral, or autonomic nervous system. Nerve modulation may take the form of nerve stimulation, which may include providing energy to the nerve to create a voltage change sufficient for the nerve to activate, or propagate an electrical signal of its own. Nerve modulation may also take the form of nerve inhibition, which may including providing energy to the nerve sufficient to prevent the nerve from propagating electrical signals. Nerve inhibition may be performed through the constant application of energy, and may also be performed through the application of enough energy to inhibit the function of the nerve for some time after the application. Other forms of neural modulation may modify the function of a nerve, causing a heightened or lessened degree of sensitivity. As referred to herein, modulation of a nerve may include modulation of an entire nerve and/or modulation of a portion of a nerve. For example, modulation of a motor neuron may be performed to affect only those portions of the neuron that are distal of the location to which energy is applied.

In patients with OSA, for example, a primary target response of nerve stimulation may include contraction of a tongue muscle (e.g., the muscle) in order to move the tongue to a position that does not block the patient's airway. In the treatment of migraine headaches, nerve inhibition may be used to reduce or eliminate the sensation of pain. In the treatment of hypertension, neural modulation may be used to increase, decrease, eliminate or otherwise modify nerve signals generated by the body to regulate blood pressure.

While embodiments of the present disclosure may be disclosed for use in patients with specific conditions, the embodiments may be used in conjunction with any patient/portion of a body where nerve modulation may be desired. That is, in addition to use in patients with OSA, migraine headaches, or hypertension, embodiments of the present disclosure may be use in many other areas, including, but not limited to: deep brain stimulation (e.g., treatment of epilepsy, Parkinson's, and depression); cardiac pace-making, stomach muscle stimulation (e.g., treatment of obesity), back pain, incontinence, menstrual pain, and/or any other condition that may be affected by neural modulation.

Figure 1:
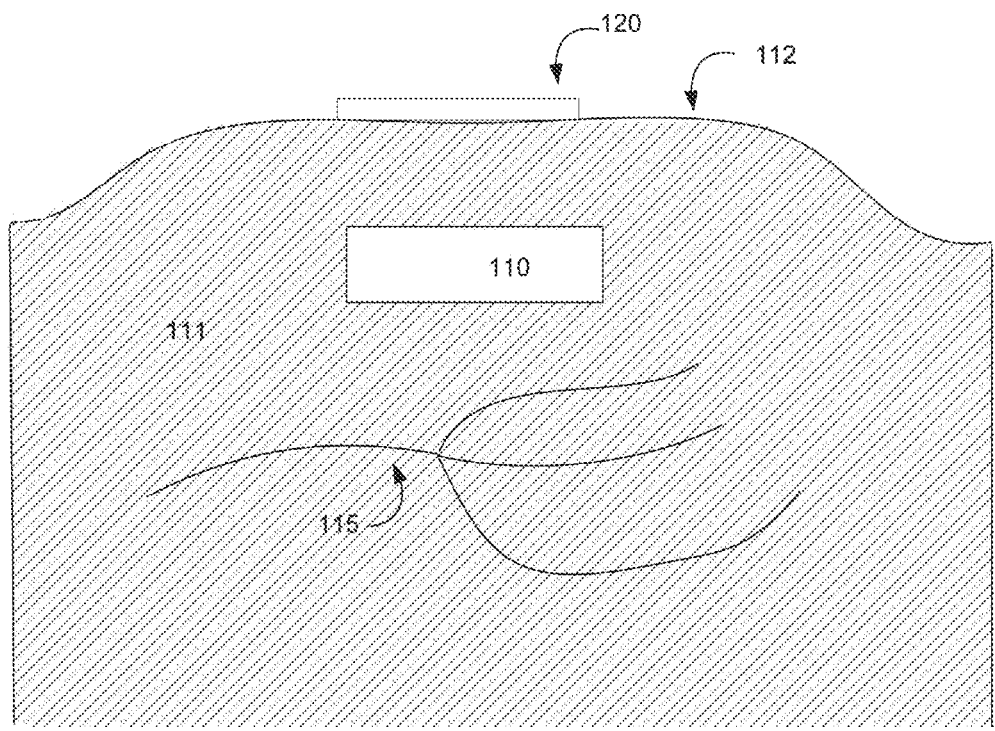
FIG. 1 schematically illustrates an implant unit and external unit, according to an exemplary embodiment of the present disclosure.

FIG. 1 illustrates an implant unit and external unit, according to an exemplary embodiment of the present disclosure. An implant unit 110, may be configured for implantation in a subject, in a location that permits it to modulate a nerve 115. The implant unit 110 may be located in a subject such that intervening tissue 111 exists between the implant unit 110 and the nerve 115. Intervening tissue may include muscle tissue, connective tissue, organ tissue, or any other type of biological tissue. Thus, location of implant unit 110 does not require contact with nerve 115 for effective neuromodulation. The implant unit 110 may also be located directly adjacent to nerve 115, such that no intervening tissue 111 exists.

In treating OSA, implant unit 110 may be located on a genioglossus muscle of a patient. Such a location is suitable for modulation of the hypoglossal nerve, branches of which run inside the genioglossus muscle. Further details regarding implantation locations of an implant unit 110 for treatment of OSA are provided below with respect to FIGS. 12 and 13. Implant unit 110 may also be configured for placement in other locations. For example, migraine treatment may require subcutaneous implantation in the back of the neck, near the hairline of a subject, or behind the ear of a subject, to modulate the greater occipital nerve, lesser occipital nerve, and/or the trigeminal nerve. Further details regarding implantation locations of an implant unit 110 for treatment of head pain, such as migraine headaches, are provided below with respect to FIG. 14. Treating hypertension may require the implantation of a neuromodulation implant intravascularly inside the renal artery or renal vein (to modulate the parasympathetic renal nerves), either unilaterally or bilaterally, inside the carotid artery or jugular vein (to modulate the glossopharyngeal nerve through the carotid baroreceptors). Alternatively or additionally, treating hypertension may require the implantation of a neuromodulation implant subcutaneously, behind the ear or in the neck, for example, to directly modulate the glossopharyngeal nerve. Further details regarding implantation locations of an implant unit 110 for treatment of hypertension are provided below, with respect to FIGS. 15 and 16.

External unit 120 may be configured for location external to a patient, either directly contacting, or close to the skin 112 of the patient. External unit 120 may be configured to be affixed to the patient, for example, by adhering to the skin 112 of the patient, or through a band or other device configured to hold external unit 120 in place. Adherence to the skin of external unit 120 may occur such that it is in the vicinity of the location of implant unit 110.

Figure 2:
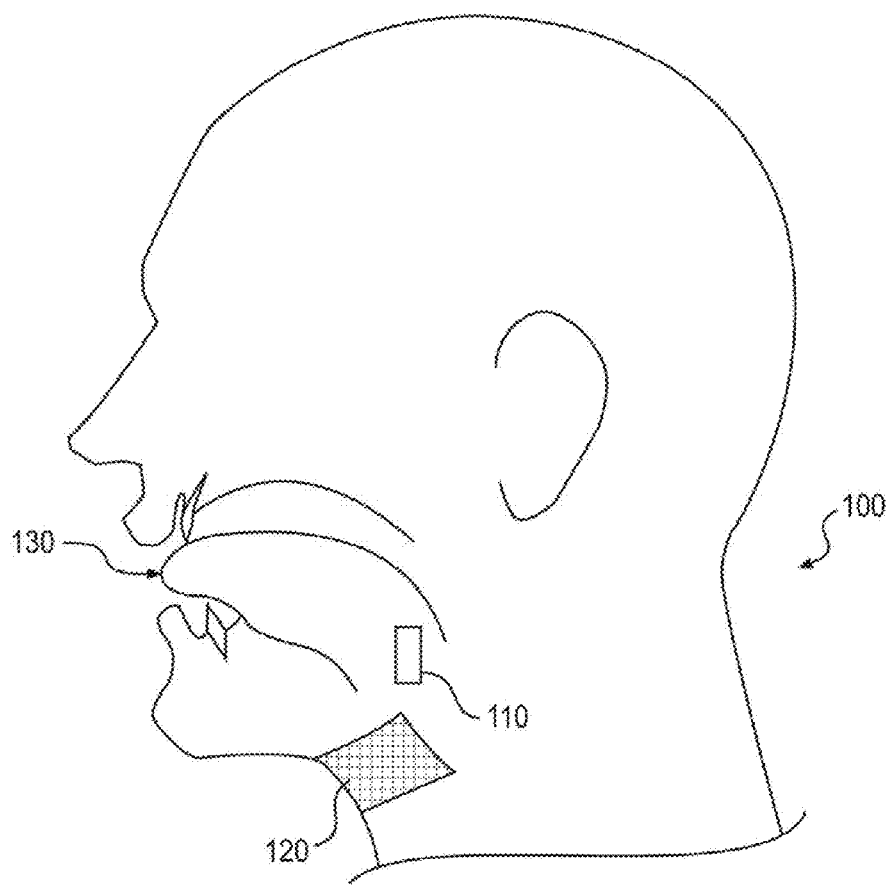
FIG. 2 is a partially cross-sectioned side view of a subject with an implant unit and external unit, according to an exemplary embodiment of the present disclosure.

FIG. 2 illustrates an exemplary embodiment of a neuromodulation system for delivering energy in a patient 100 with OSA. The system may include an external unit 120 that may be configured for location external to the patient. As illustrated in FIG. 2, external unit 120 may be configured to be affixed to the patient 100. FIG. 2 illustrates that in a patient 100 with OSA, the external unit 120 may be configured for placement underneath the patient's chin and/or on the front of patient's neck. The suitability of placement locations may be determined by communication between external unit 120 and implant unit 110, discussed in greater detail below. In alternate embodiments, for the treatment of conditions other than OSA, the external unit may be configured to be affixed anywhere suitable on a patient, such as the back of a patient's neck, i.e. for communication with a migraine treatment implant unit, on the outer portion of a patient's abdomen, i.e. for communication with a stomach modulating implant unit, on a patient's back, i.e. for communication with a renal artery modulating implant unit, and/or on any other suitable external location on a patient's skin, depending on the requirements of a particular application.

External unit 120 may further be configured to be affixed to an alternative location proximate to the patient. For example, in one embodiment, the external unit may be configured to fixedly or removably adhere to a strap or a band that may be configured to wrap around a part of a patient's body. Alternatively, or in addition, the external unit may be configured to remain in a desired location external to the patient's body without adhering to that location.

The external unit 120 may include a housing. The housing may include any suitable container configured for retaining components. In addition, while the external unit is illustrated schematically in FIG. 2, the housing may be any suitable size and/or shape and may be rigid or flexible. Non-limiting examples of housings for the external unit 100 include one or more of patches, buttons, or other receptacles having varying shapes and dimensions and constructed of any suitable material. In one embodiment, for example, the housing may include a flexible material such that the external unit may be configured to conform to a desired location. For example, as illustrated in FIG. 2, the external unit may include a skin patch, which, in turn, may include a flexible substrate. The material of the flexible substrate may include, but is not limited to, plastic, silicone, woven natural fibers, and other suitable polymers, copolymers, and combinations thereof. Any portion of external unit 120 may be flexible or rigid, depending on the requirements of a particular application.

As previously discussed, in some embodiments external unit 120 may be configured to adhere to a desired location. Accordingly, in some embodiments, at least one side of the housing may include an adhesive material. The adhesive material may include a biocompatible material and may allow for a patient to adhere the external unit to the desired location and remove the external unit upon completion of use. The adhesive may be configured for single or multiple uses of the external unit. Suitable adhesive materials may include, but are not limited to biocompatible glues, starches, elastomers, thermoplastics, and emulsions.

Figure 3:
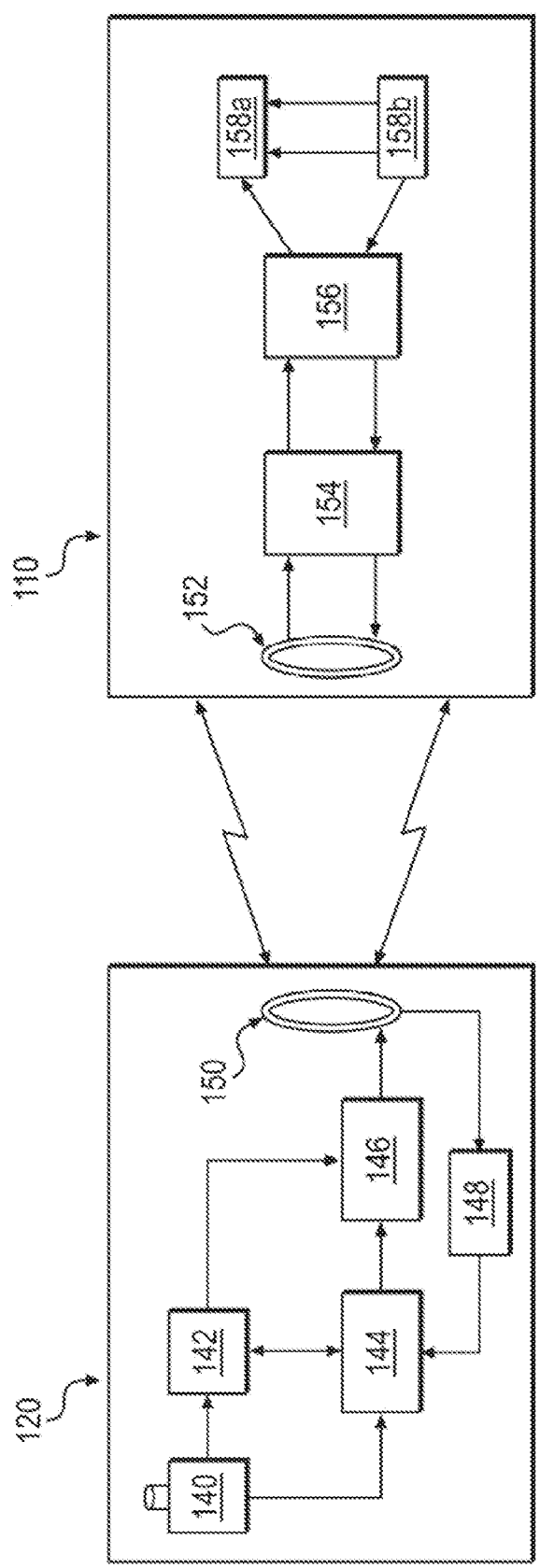
FIG. 3 schematically illustrates a system including an implant unit and an external unit, according to an exemplary embodiment of the present disclosure.

FIG. 3 schematically illustrates a system including external unit 120 and an implant unit 110. In some embodiments, implant unit 110 may be configured as a unit to be implanted into the body of a patient, and external unit 120 may be configured to send signals to and/or receive signals from implant unit 110.

As shown in FIG. 3, various components may be included within a housing of external unit 120 or otherwise associated with external unit 120. As illustrated in FIG. 3, at least one processor 144 may be associated with external unit 120. For example, the at least one processor 144 may be located within the housing of external unit 120. In alternative embodiments, the at least one processor may be configured for wired or wireless communication with the external unit from a location external to the housing.

The at least one processor may include any electric circuit that may be configured to perform a logic operation on at least one input variable. The at least one processor may therefore include one or more integrated circuits, microchips, microcontrollers, and microprocessors, which may be all or part of a central processing unit (CPU), a digital signal processor (DSP), a field programmable gate array (FPGA), or any other circuit known to those skilled in the art that may be suitable for executing instructions or performing logic operations.

FIG. 3 illustrates that the external unit 120 may further be associated with a power source 140. The power source may be removably couplable to the external unit at an exterior location relative to external unit. Alternatively, as shown in FIG. 3, power source 140 may be permanently or removably coupled to a location within external unit 120. The power source may further include any suitable source of power configured to be in electrical communication with the processor. In one embodiment, for example the power source 140 may include a battery.

The power source may be configured to power various components within the external unit. As illustrated in FIG. 3, power source 140 may be configured to provide power to the processor 144. In addition, the power source 140 may be configured to provide power to a signal source 142. The signal source 142 may be in communication with the processor 144 and may include any device configured to generate a signal (e.g., a sinusoidal signal, square wave, triangle wave, microwave, radio-frequency (RF) signal, or any other type of electromagnetic signal). Signal source 142 may include, but is not limited to, a waveform generator that may be configured to generate alternating current (AC) signals and/or direct current (DC) signals. In one embodiment, for example, signal source 142 may be configured to generate an AC signal for transmission to one or more other components. Signal source 142 may be configured to generate a signal of any suitable frequency. In some embodiments, signal source 142 may be configured to generate a signal having a frequency of from about 6.5 MHz to about 13.6 MHz. In additional embodiments, signal source 142 may be configured to generate a signal having a frequency of from about 7.4 to about 8.8 MHz. In further embodiments, signal source 142 may generate a signal having a frequency as low as 90 kHz or as high as 28 MHz.

Signal source 142 may be configured for direct or indirect electrical communication with an amplifier 146. The amplifier may include any suitable device configured to amplify one or more signals generated from signal source 142. Amplifier 146 may include one or more of various types of amplification devices, including, for example, transistor based devices, operational amplifiers, RF amplifiers, power amplifiers, or any other type of device that can increase the gain associated one or more aspects of a signal. The amplifier may further be configured to output the amplified signals to one or more components within external unit 120.

The external unit may additionally include a primary antenna 150. The primary antenna may be configured as part of a circuit within external unit 120 and may be coupled either directly or indirectly to various components in external unit 120. For example, as shown in FIG. 3, primary antenna 150 may be configured for communication with the amplifier 146.

The primary antenna may include any conductive structure that may be configured to create an electromagnetic field. The primary antenna may further be of any suitable size, shape, and/or configuration. The size, shape, and/or configuration may be determined by the size of the patient, the placement location of the implant unit, the size and/or shape of the implant unit, the amount of energy required to modulate a nerve, a location of a nerve to be modulated, the type of receiving electronics present on the implant unit, etc. The primary antenna may include any suitable antenna known to those skilled in the art that may be configured to send and/or receive signals. Suitable antennas may include, but are not limited to, a long-wire antenna, a patch antenna, a helical antenna, etc. In one embodiment, for example, as illustrated in FIG. 3, primary antenna 150 may include a coil antenna. Such a coil antenna may be made from any suitable conductive material and may be configured to include any suitable arrangement of conductive coils (e.g., diameter, number of coils, layout of coils, etc.). A coil antenna suitable for use as primary antenna 150 may have a diameter of between about 1 cm and 10 cm, and may be circular or oval shaped. In some embodiments, a coil antenna may have a diameter between 5 cm and 7 cm, and may be oval shaped. A coil antenna suitable for use as primary antenna 150 may have any number of windings, e.g. 4, 8, 12, or more. A coil antenna suitable for use as primary antenna 150 may have a wire diameter between about 0.1 mm and 2 mm. These antenna parameters are exemplary only, and may be adjusted above or below the ranges given to achieve suitable results.

As noted, implant unit 110 may be configured to be implanted in a patient's body (e.g., beneath the patient's skin). FIG. 2 illustrates that the implant unit 110 may be configured to be implanted for modulation of a nerve associated with a muscle of the subject's tongue 130. Modulating a nerve associated with a muscle of the subject's tongue 130 may include stimulation to cause a muscle contraction. In further embodiments, the implant unit may be configured to be placed in conjunction with any nerve that one may desire to modulate. For example, modulation of the occipital nerve, the greater occipital nerve, and/or the trigeminal nerve may be useful for treating pain sensation in the head, such as that from migraines. Modulation of parasympathetic nerve fibers on and around the renal arteries (i.e. the renal nerves), the vagus nerve, and/or the glossopharyngeal nerve may be useful for treating hypertension. Additionally, any nerve of the peripheral nervous system (both spinal and cranial), including motor neurons, sensory neurons, sympathetic neurons and parasympathetic neurons, may be modulated to achieve a desired effect.

Implant unit 110 may be formed of any materials suitable for implantation into the body of a patient. In some embodiments, implant unit 110 may include a flexible carrier 161 (FIG. 4) including a flexible, biocompatible material. Such materials may include, for example, silicone, polyimides, phenyltrimethoxysilane (PTMS), polymethyl methacrylate (PMMA), Parylene C, polyimide, liquid polyimide, laminated polyimide, black epoxy, polyether ether ketone (PEEK), Liquid Crystal Polymer (LCP), Kapton, etc. Implant unit 110 may further include circuitry including conductive materials, such as gold, platinum, titanium, or any other biocompatible conductive material or combination of materials. Implant unit 110 and flexible carrier 161 may also be fabricated with a thickness suitable for implantation under a patient's skin. Implant 110 may have thickness of less than about 4 mm or less than about 2 mm.

Other components that may be included in or otherwise associated with the implant unit are illustrated in FIG. 3. For example, implant unit 110 may include a secondary antenna 152 mounted onto or integrated with flexible carrier 161. Similar to the primary antenna, the secondary antenna may include any suitable antenna known to those skilled in the art that may be configured to send and/or receive signals. The secondary antenna may include any suitable size, shape, and/or configuration. The size, shape and/or configuration may be determined by the size of the patient, the placement location of the implant unit, the amount of energy required to modulate the nerve, etc. Suitable antennas may include, but are not limited to, a long-wire antenna, a patch antenna, a helical antenna, etc. In some embodiments, for example, secondary antenna 152 may include a coil antenna having a circular shape (see also FIG. 4) or oval shape. Such a coil antenna may be made from any suitable conductive material and may be configured to include any suitable arrangement of conductive coils (e.g., diameter, number of coils, layout of coils, etc.). A coil antenna suitable for use as secondary antenna 152 may have a diameter of between about 5 mm and 30 mm, and may be circular or oval shaped. A coil antenna suitable for use as secondary antenna 152 may have any number of windings, e.g. 4, 15, 20, 30, or 50. A coil antenna suitable for use as secondary antenna 152 may have a wire diameter between about 0.01 mm and 1 mm. These antenna parameters are exemplary only, and may be adjusted above or below the ranges given to achieve suitable results.

Figure 4:
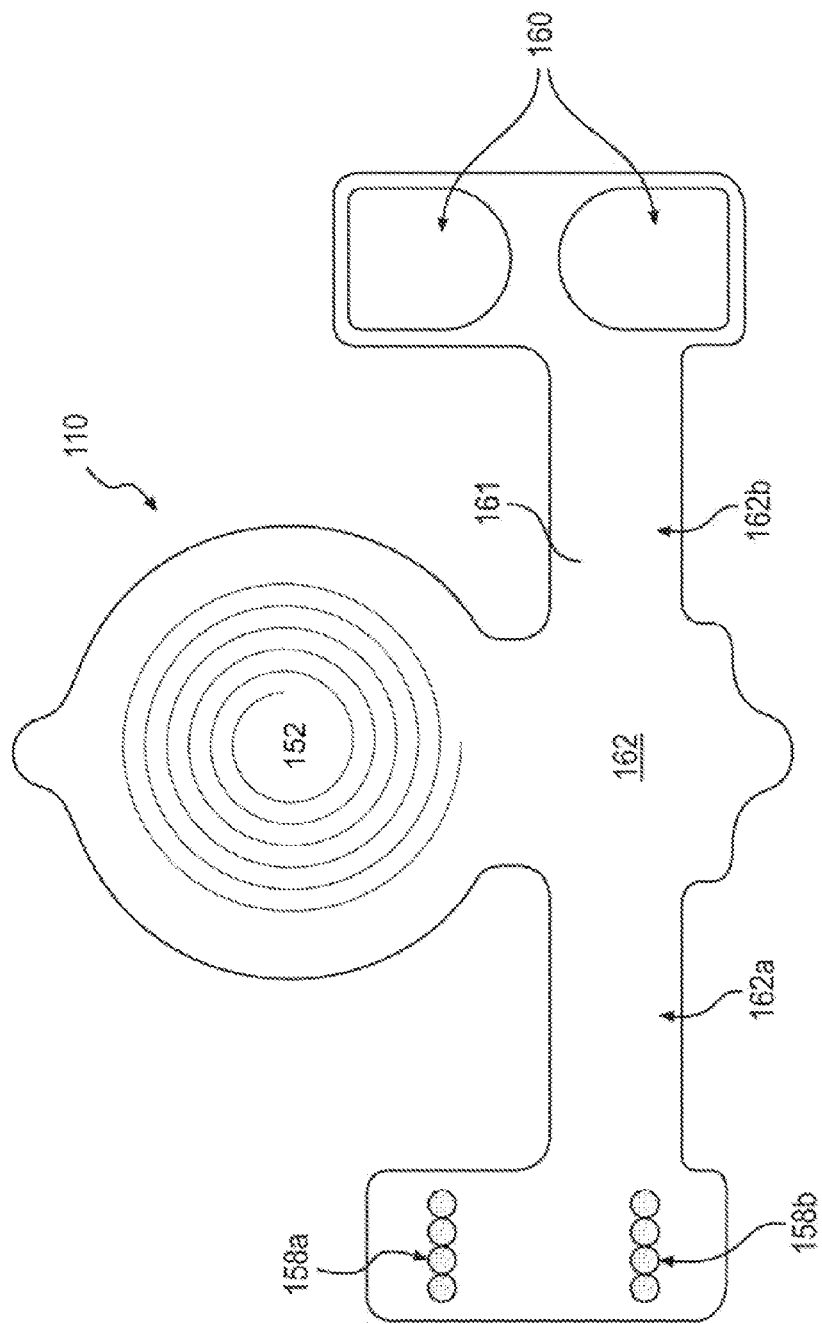
FIG. 4 is a top view of an implant unit, according to an exemplary embodiment of the present disclosure.

Implant unit 110 may additionally include a plurality of field-generating implant electrodes 158*a*, 158*b*. The electrodes may include any suitable shape and/or orientation on the implant unit so long as the electrodes may be configured to generate an electric field in the body of a patient. Like implant unit 110, implant electrodes 158a and 158b may be configured for implantation into the body of a subject in the vicinity of one or more nerves. Implant electrodes 158a and 158b may also include any suitable conductive material (e.g., copper, silver, gold, platinum, iridium, platinum-iridium, platinum-gold, conductive polymers, etc.) or combinations of conductive (and/or noble metals) materials. In some embodiments, for example, the electrodes may include short line electrodes, point electrodes, circular electrodes, and/or circular pairs of electrodes. As shown in FIG. 4, electrodes 158a and 158b may be located on an end of a first extension 162a of an elongate arm 162. The electrodes, however, may be located on any portion of implant unit 110. Additionally, implant unit 110 may include electrodes located at a plurality of locations, for example on an end of both a first extension 162a and a second extension 162b of elongate arm 162, as illustrated, for example, in FIG. 5. Electrodes on different sides of implant unit 110 may be activated sequentially or simultaneously to generate respective electric fields. Implant electrodes 158a and 158b may be spaced from one another along the longitudinal direction of a nerve to be modulated. Implant electrodes may have a thickness between about 200 nanometers and 1 millimeter, and may have a surface area of about 0.01 mm$^2$ to about 80 mm$^2$. Anode and cathode electrode pairs may be spaced apart by about a distance of about 0.2 mm to 25 mm. In additional embodiments, anode and cathode electrode pairs may be spaced apart by a distance of about 1 mm to 10 mm, or between 4 mm and 7 mm. In other embodiments, anode and cathode electrode pairs may be spaced apart by a distance of approximately 6 mm. Adjacent anodes or adjacent cathodes may be spaced apart by distances as small as 0.001 mm or less, or as great as 25 mm or more. In some embodiments, adjacent anodes or adjacent cathodes may be spaced apart by a distance between about 0.2 mm and 1 mm.

FIG. 4 provides a schematic representation of an exemplary configuration of implant unit 110. As illustrated in FIG. 4, in one embodiment, the field-generating electrodes 158a and 158b may include two sets of four circular electrodes, provided on flexible carrier 161, with one set of electrodes providing an anode and the other set of electrodes providing a cathode. Implant unit 110 may include one or more structural elements to facilitate implantation of implant unit 110 into the body of a patient. Such elements may include, for example, elongated arms, suture holes, polymeric surgical mesh, biological glue, spikes of flexible carrier protruding to anchor to the tissue, spikes of additional biocompatible material for the same purpose, etc. that facilitate alignment of implant unit 110 in a desired orientation within a patient's body and provide attachment points for securing implant unit 110 within a body. For example, in some embodiments, implant unit 110 may include an elongate arm 162 having a first extension 162a and, optionally, a second extension 162b. Extensions 162a and 162b may aid in orienting implant unit 110 with respect to a particular muscle (e.g., the genioglossus muscle), a nerve within a patient's body, or a surface within a body above a nerve. For example, first and second extensions 162a, 162b may be configured to enable the implant unit to conform at least partially around soft or hard tissue (e.g., nerve, bone, or muscle, etc.) beneath a patient's skin. Further, implant unit 110 may also include one or more suture holes 160 located anywhere on flexible carrier 161. For example, in some embodiments, suture holes 160 may be placed on second extension 162b of elongate arm 162 and/or on first extension 162a of elongate arm 162. Implant unit 110 may be constructed in various shapes. In some embodiments, implant unit may appear substantially as illustrated in FIG. 4. In other embodiments, implant unit 110 may lack illustrated structures such as second extension 162b, or may have additional or different structures in different orientations. Additionally, implant unit 110 may be formed with a generally triangular, circular, or rectangular shape, as an alternative to the winged shape shown in FIG. 4. In some embodiments, the shape of implant unit 110 (e.g., as shown in FIG. 4) may facilitate orientation of implant unit 110 with respect to a particular nerve to be modulated. Thus, other regular or irregular shapes may be adopted in order to facilitate implantation in differing parts of the body. For example, flexible carrier 161 may facilitate orientation of implant unit 110 with respect to the contour of a particular tissue. Such tissue may include any combination of muscle tissue, bone, connective tissue, adipose tissue, or organ tissue. For subjects suffering from obstructive sleep apnea, for instance, implant unit 110 may be configured to adapt to the contour of the genioglossus muscle.

As illustrated in FIG. 4, secondary antenna 152, circuitry 180, and electrodes 158a, 158b may be mounted on or integrated with flexible carrier 161. Various circuit components and connecting wires (discussed further below) may be used to connect secondary antenna with implant electrodes 158a and 158b. To protect the antenna, electrodes, circuit components, and connecting wires from the environment within a patient's body, implant unit 110 may include a protective coating that encapsulates implant unit 110. In some embodiments, the protective coating may be made from a flexible material to enable bending along with flexible carrier 161. The encapsulation material of the protective coating may also resist humidity penetration and protect against corrosion. In some embodiments, the protective coating may include silicone, polyimides, phenyltrimethoxysilane (PTMS), polymethyl methacrylate (PMMA), Parylene C, liquid polyimide, laminated polyimide, polyimide, Kapton, black epoxy, polyether ketone (PEEK), Liquid Crystal Polymer (LCP), or any other suitable biocompatible coating. In some embodiments, the protective coating may include a plurality of layers, including different materials or combinations of materials in different layers.

Figure 5:
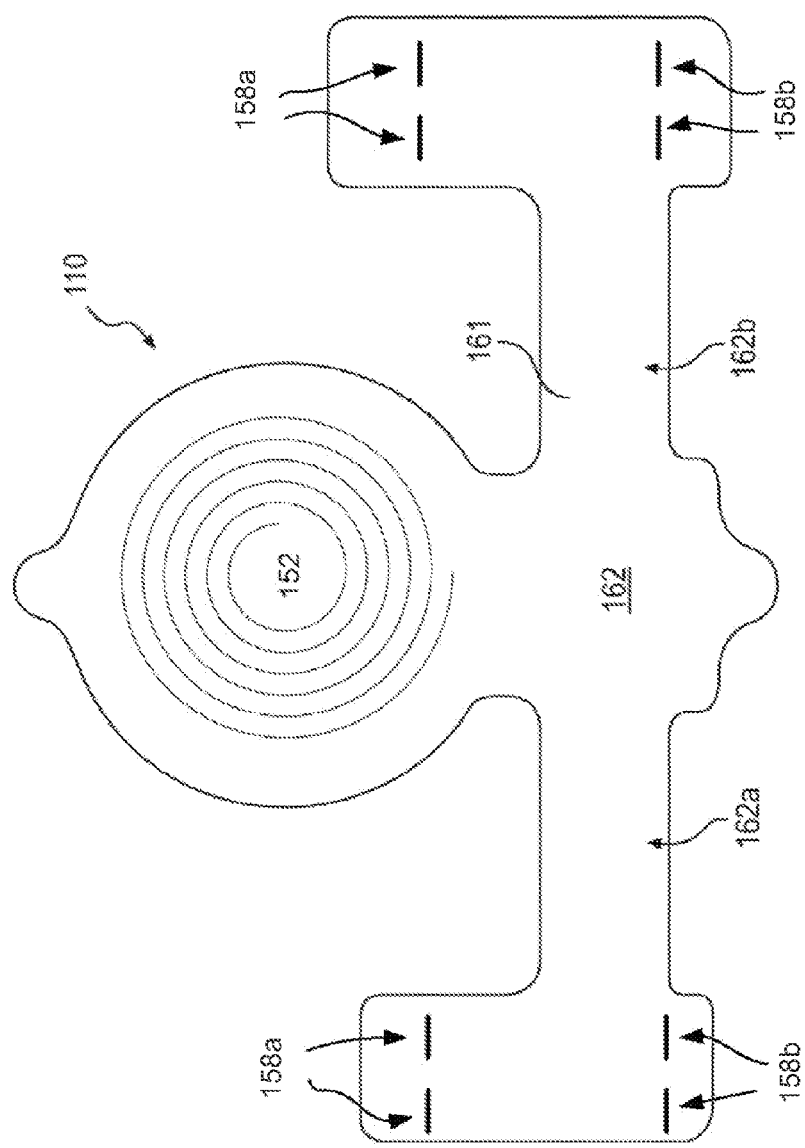
FIG. 5 is a top view of an alternate embodiment of an implant unit, according to an exemplary embodiment of the present disclosure.

FIG. 5 is a perspective view of an alternate embodiment of an implant unit 110, according to an exemplary embodiment of the present disclosure. As illustrated in FIG. 5, implant unit 110 may include a plurality of electrodes, located, for example, at the ends of first extension 162a and second extension 162b. FIG. 5 illustrates an embodiment wherein implant electrodes 158a and 158b include short line electrodes.

Returning to FIGS. 2 and 3, external unit 120 may be configured to communicate with implant unit 110. For example, in some embodiments, a primary signal may be generated on primary antenna 150, using, e.g., processor 144, signal source 142, and amplifier 146. More specifically, in one embodiment, power source 140 may be configured to provide power to one or both of the processor 144 and the signal source 142. The processor 144 may be configured to cause signal source 142 to generate a signal (e.g., an RF energy signal). Signal source 142 may be configured to output the generated signal to amplifier 146, which may amplify the signal generated by signal source 142. The amount of amplification and, therefore, the amplitude of the signal may be controlled, for example, by processor 144. The amount of gain or amplification that processor 144 causes amplifier 146 to apply to the signal may depend on a variety of factors, including, but not limited to, the shape, size, and/or configuration of primary antenna 150, the size of the patient, the location of implant unit 110 in the patient, the shape, size, and/or configuration of secondary antenna 152, a degree of coupling between primary antenna 150 and secondary antenna 152 (discussed further below), a desired magnitude of electric field to be generated by implant electrodes 158a, 158b, etc. Amplifier 146 may output the amplified signal to primary antenna 150.

External unit 120 may communicate a primary signal on primary antenna to the secondary antenna 152 of implant unit 110. This communication may result from coupling between primary antenna 150 and secondary antenna 152. Such coupling of the primary antenna and the secondary antenna may include any interaction between the primary antenna and the secondary antenna that causes a signal on the secondary antenna in response to a signal applied to the primary antenna. In some embodiments, coupling between the primary and secondary antennas may include capacitive coupling, inductive coupling, radiofrequency coupling, etc. and any combinations thereof.

Coupling between primary antenna 150 and secondary antenna 152 may depend on the proximity of the primary antenna relative to the secondary antenna. That is, in some embodiments, an efficiency or degree of coupling between primary antenna 150 and secondary antenna 152 may depend on the proximity of the primary antenna to the secondary antenna. The proximity of the primary and secondary antennas may be expressed in terms of a coaxial offset (e.g., a distance between the primary and secondary antennas when central axes of the primary and secondary antennas are co-aligned), a lateral offset (e.g., a distance between a central axis of the primary antenna and a central axis of the secondary antenna), and/or an angular offset (e.g., an angular difference between the central axes of the primary and secondary antennas). In some embodiments, a theoretical maximum efficiency of coupling may exist between primary antenna 150 and secondary antenna 152 when both the coaxial offset, the lateral offset, and the angular offset are zero. Increasing any of the coaxial offset, the lateral offset, and the angular offset may have the effect of reducing the efficiency or degree of coupling between primary antenna 150 and secondary antenna 152.

As a result of coupling between primary antenna 150 and secondary antenna 152, a secondary signal may arise on secondary antenna 152 when the primary signal is present on the primary antenna 150. Such coupling may include inductive/magnetic coupling, RF coupling/transmission, capacitive coupling, or any other mechanism where a secondary signal may be generated on secondary antenna 152 in response to a primary signal generated on primary antenna 150. Coupling may refer to any interaction between the primary and secondary antennas. In addition to the coupling between primary antenna 150 and secondary antenna 152, circuit components associated with implant unit 110 may also affect the secondary signal on secondary antenna 152. Thus, the secondary signal on secondary antenna 152 may refer to any and all signals and signal components present on secondary antenna 152 regardless of the source.

While the presence of a primary signal on primary antenna 150 may cause or induce a secondary signal on secondary antenna 152, the coupling between the two antennas may also lead to a coupled signal or signal components on the primary antenna 150 as a result of the secondary signal present on secondary antenna 152. A signal on primary antenna 150 induced by a secondary signal on secondary antenna 152 may be referred to as a primary coupled signal component. The primary signal may refer to any and all signals or signal components present on primary antenna 150, regardless of source, and the primary coupled signal component may refer to any signal or signal component arising on the primary antenna as a result of coupling with signals present on secondary antenna 152. Thus, in some embodiments, the primary coupled signal component may contribute to the primary signal on primary antenna 150.

Implant unit 110 may be configured to respond to external unit 120. For example, in some embodiments, a primary signal generated on primary coil 150 may cause a secondary signal on secondary antenna 152, which in turn, may cause one or more responses by implant unit 110. In some embodiments, the response of implant unit 110 may include the generation of an electric field between implant electrodes 158a and 158b.

Figure 6:
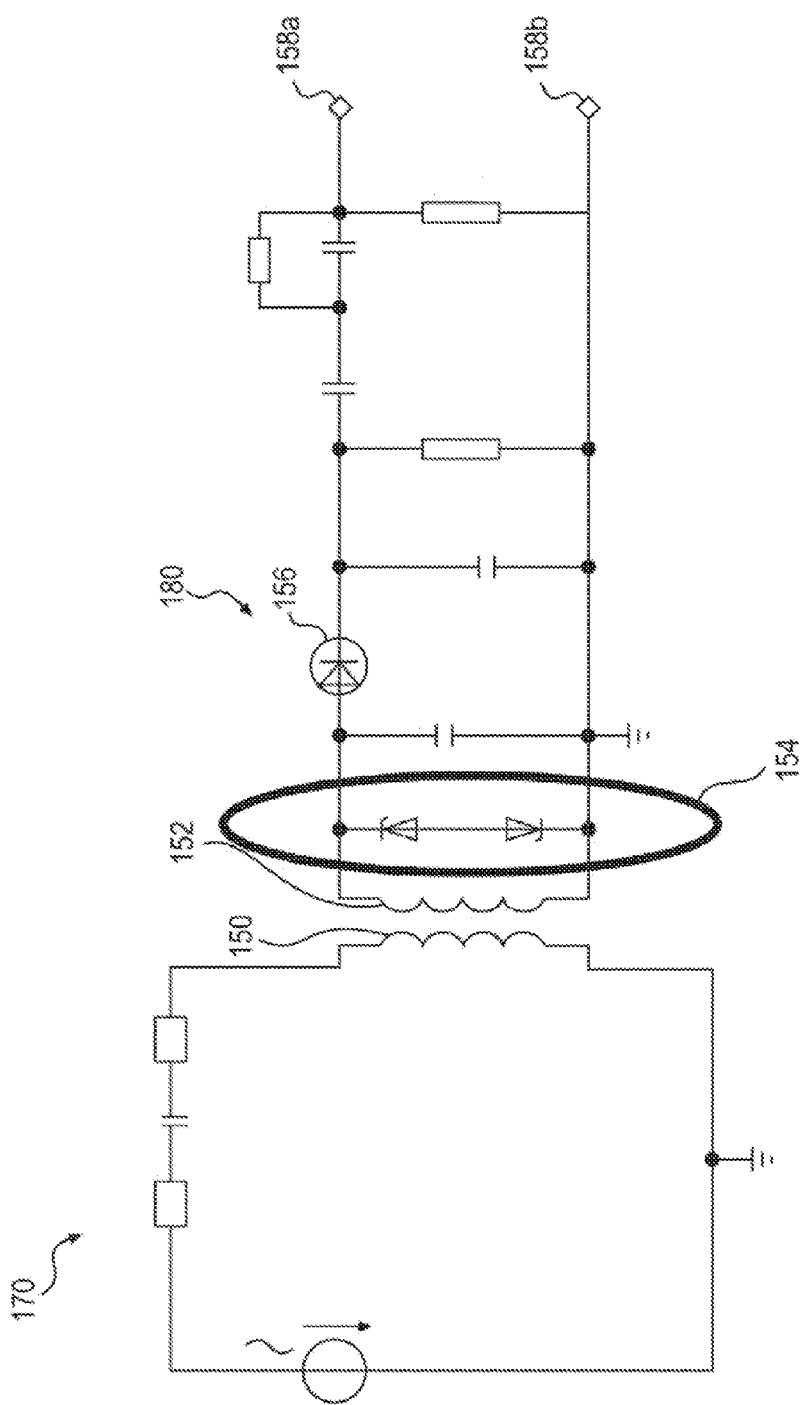
FIG. 6 illustrates circuitry of an implant unit and an external unit, according to an exemplary embodiment of the present disclosure.

FIG. 6 illustrates circuitry 170 that may be included in external unit 120 and circuitry 180 that may be included in implant unit 110. Additional, different, or fewer circuit components may be included in either or both of circuitry 170 and circuitry 180. As shown in FIG. 6, secondary antenna 152 may be arranged in electrical communication with implant electrodes 158a, 158b. In some embodiments, circuitry 180 connecting secondary antenna 152 with implant electrodes 158a and 158b may cause a voltage potential across implant electrodes 158a and 158b in the presence of a secondary signal on secondary antenna 152. For example, an implant unit 110 may apply a voltage potential to implant electrodes 158a and 158b in response to an AC signal received by secondary antenna 152. As used herein, the term "voltage potential" may include a voltage signal or any electrical signal. This voltage potential may be referred to as a field inducing signal, as this voltage potential may generate an electric field between implant electrodes 158a and 158b. More broadly, the field inducing signal may include any signal (e.g., voltage potential) applied to electrodes associated with the implant unit that may result in an electric field being generated between the electrodes.

The field inducing signal may be generated as a result of conditioning of the secondary signal by circuitry 180. As shown in FIG. 6, circuitry 170 of external unit 120 may be configured to generate an AC primary signal on primary antenna 150 that may cause an AC secondary signal on secondary antenna 152 in circuitry 180. In certain embodiments, however, it may be advantageous (e.g., in order to generate a unidirectional electric field for modulation of a nerve) to provide a DC field inducing signal at implant electrodes 158a and 158b. To convert the AC secondary signal on secondary antenna 152 to a DC field inducing signal, circuitry 180 in implant unit 110 may include an AC-DC converter. The AC to DC converter may include any suitable converter known to those skilled in the art. For example, in some embodiments the AC-DC converter may include rectification circuit components including, for example, diode 156 and appropriate capacitors and resistors. In alternative embodiments, implant unit 110 may include an AC-AC converter, or no converter, in order to provide an AC field inducing signal at implant electrodes 158a and 158b.

As noted above, the field inducing signal may be configured to generate an electric field between implant electrodes 158a and 158b. In some instances, the magnitude, orientation, and/or duration of the generated electric field resulting from the field inducing signal may be sufficient to modulate one or more nerves in the vicinity of electrodes 158a and 158b. In such cases, the field inducing signal may be referred to as a modulation signal. In other instances, the magnitude and/or duration of the field inducing signal may generate an electric field that does not result in nerve modulation. In such cases, the field inducing signal may be referred to as a sub-modulation signal.

Various types of field inducing signals may constitute modulation signals. For example, in some embodiments, a modulation signal may include a moderate amplitude and moderate duration, while in other embodiments, a modulation signal may include a higher amplitude and a shorter duration. Various amplitudes and/or durations of field-inducing signals across electrodes 158a, 158b may result in modulation signals, and whether a field-inducing signal rises to the level of a modulation signal can depend on many factors (e.g., distance from a particular nerve to be stimulated; whether the nerve is branched; orientation of the induced electric field with respect to the nerve; type of tissue present between the electrodes and the nerve; etc.).

Whether a field inducing signal constitutes a modulation signal may also depend on the orientation of the electrodes 158a and 158b and the corresponding electric field. In response to a field inducing signal, implant electrodes 158a and 158b may be configured to generate an electric field with field lines extending generally in the longitudinal direction of one or more nerves to be modulated. In some embodiments, implant electrodes 158a and 158b may be spaced apart from one another along the longitudinal direction of a nerve to facilitate generation of such an electric field. The electric field may also be configured to extend in a direction substantially parallel to a longitudinal direction of at least some portion of the nerve to be modulated. For example, a substantially parallel field may include field lines that extend more in a longitudinal direction than a transverse direction compared to the nerve. Orienting the electric field in this way may facilitate electrical current flow through a nerve or tissue, thereby increasing the likelihood of eliciting an action potential to induce modulation.

FIG. 10a illustrates a pair of electrodes 158a, 158b spaced apart from one another along the longitudinal direction of nerve 210 to facilitate generation of an electric field having field lines 220 substantially parallel to the longitudinal direction of nerve 210. In FIG. 10a, modulation electrodes 158a, 158b are illustrated as line electrodes, although the generation of substantially parallel electric fields may be accomplished through the use of other types of electrodes, including, for example, a series of point electrodes. Utilizing an electric field having field lines 220 extending in a longitudinal direction of nerve 210 may serve to reduce the amount of energy required to achieve neural modulation.

Naturally functioning neurons function by transmitting action potentials along their length. Structurally, neurons include multiple ion channels along their length that serve to maintain a voltage potential gradient across a plasma membrane between the interior and exterior of the neuron. Ion channels operate by maintaining an appropriate balance between positively charged sodium ions inside on one side of the plasma membrane and negatively charged potassium ions on the other side of the plasma membrane. A sufficiently high voltage potential difference created near an ion channel may exceed a membrane threshold potential of the ion channel. The ion channel may then be induced to activate, pumping the sodium and potassium ions across the plasma membrane to switch places in the vicinity of the activated ion channel. This, in turn, further alters the potential difference in the vicinity of the ion channel, which may serve to activate a neighboring ion channel. The cascading activation of adjacent ion channels may serve to propagate an action potential along the length of the neuron. Further, the activation of an ion channel in an individual neuron may induce the activation of ion channels in neighboring neurons that, bundled together, form nerve tissue. The activation of a single ion channel in a single neuron, however, may not be sufficient to induce the cascading activation of neighboring ion channels necessary to permit the propagation of an action potential. Thus, the more ion channels in a locality that may be recruited by an initial potential difference, caused through natural means such as the action of nerve endings or through artificial means, such as the application of electric fields, the more likely the propagation of an action potential may be. The process of artificially inducing the propagation of action potentials along the length of a nerve may be referred to as stimulation, or up modulation.

Neurons may also be prevented from functioning naturally through constant or substantially constant application of a voltage potential difference. After activation, each ion channel experiences a refractory period, during which it "resets" the sodium and potassium concentrations across the plasma membrane back to an initial state. Resetting the sodium and potassium concentrations causes the membrane threshold potential to return to an initial state. Until the ion channel restores an appropriate concentration of sodium and potassium across the plasma membrane, the membrane threshold potential will remain elevated, thus requiring a higher voltage potential to cause activation of the ion channel. If the membrane threshold potential is maintained at a high enough level, action potentials propagated by neighboring ion channels may not create a large enough voltage potential difference to surpass the membrane threshold potential and activate the ion channel. Thus, by maintaining a sufficient voltage potential difference in the vicinity of a particular ion channel, that ion channel may serve to block further signal transmission. The membrane threshold potential may also be raised without eliciting an initial activation of the ion channel. If an ion channel (or a plurality of ion channels) are subjected to an elevated voltage potential difference that is not high enough to surpass the membrane threshold potential, it may serve to raise the membrane threshold potential over time, thus having a similar effect to an ion channel that has not been permitted to properly restore ion concentrations. Thus, an ion channel may be recruited as a block without actually causing an initial action potential to propagate. This method may be valuable, for example, in pain management, where the propagation of pain signals is undesired. As described above with respect to stimulation, the larger the number of ion channels in a locality that may be recruited to serve as blocks, the more likely the chance that an action potential propagating along the length of the nerve will be blocked by the recruited ion channels, rather than traveling through neighboring, unblocked channels.

The number of ion channels recruited by an voltage potential difference may be increased in at least two ways. First, more ion channels may be recruited by utilizing a larger voltage potential difference in a local area. Second, more ion channels may be recruited by expanding the area affected by the voltage potential difference.

Returning to FIG. 10a, it can be seen that, due to the electric field lines 220 running in a direction substantially parallel to the longitudinal direction of the nerve 210, a large portion of nerve 210 may encounter the field. Thus, more ion channels from the neurons that make up nerve 210 may be recruited without using a larger voltage potential difference. In this way, modulation of nerve 210 may be achieved with a lower current and less power usage. FIG. 10b illustrates an embodiment wherein electrodes 158a and 158 are still spaced apart from one another in a longitudinal direction of at least a portion of nerve 210. A significant portion of nerve 210 remains inside of the electric field. FIG. 10c illustrates a situation wherein electrodes 158a and 158b are spaced apart from one another in a transverse direction of nerve 210. In this illustration, it can be seen that a significantly smaller portion of nerve 210 will be affected by electric field lines 220.

Figure 11:
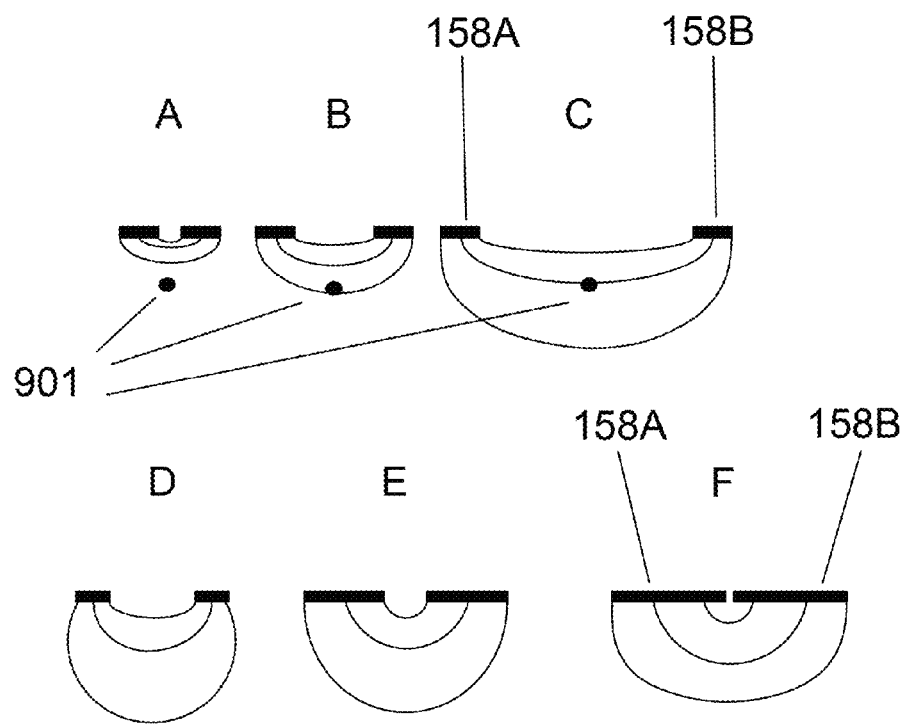
FIG. 11 illustrates affects of electrode configuration on the shape of a generated electric field.

FIG. 11 illustrates potential effects of electrode configuration on the shape of a generated electric field. The top row of electrode configurations, e.g. A, B, and C, illustrates the effects on the electric field shape when a distance between electrodes of a constant size is adjusted. The bottom row of electrode configurations, e.g. D, E, and F illustrates the effects on the electric field shape when the size of electrodes of constant distance is adjusted.

In embodiments consistent with the present disclosure, modulation electrodes 158a, 158b may be arranged on the surface of a muscle or other tissue, in order to modulate a nerve embedded within the muscle or other tissue. Thus, tissue may be interposed between modulation electrodes 158a, 158b and a nerve to be modulated. Modulation electrodes 158a, 158b may be spaced away from a nerve to be modulated. The structure and configuration of modulation electrodes 158a, 158b may play an important role in determining whether modulation of a nerve, which is spaced a certain distance away from the electrodes, may be achieved.

Electrode configurations A, B, and C show that when modulation electrodes 158a, 158b of a constant size are moved further apart, the depth of the electric field facilitated by the electrodes increases. The strength of the electric field for a given configuration may vary significantly depending on a location within the field. If a constant level of current is passed between modulation electrodes 158a and 158b, however, the larger field area of configuration C may exhibit a lower overall current density than the smaller field area of configuration A. A lower current density, in turn, implies a lower voltage potential difference between two points spaced equidistant from each other in the field facilitated by configuration C relative to that of the field facilitated by configuration A. Thus, while moving modulation electrodes 158a and 158b farther from each other increases the depth of the field, it also decreases the strength of the field. In order to modulate a nerve spaced away from modulation electrodes 158a, 158b, a distance between the electrodes may be selected in order to facilitate an electric field of strength sufficient to surpass a membrane threshold potential of the nerve (and thereby modulate it) at the depth of the nerve. If modulation electrodes 158a, 158b are too close together, the electric field may not extend deep enough into the tissue in order to modulate a nerve located therein. If modulation electrodes 158a, 158b are too far apart, the electric field may be too weak to modulate the nerve at the appropriate depth.

Appropriate distances between modulation electrodes 158a, 158b, may depend on an implant location and a nerve to be stimulated. For example, modulation point 901 is located at the same depth equidistant from the centers of modulation electrodes 158a, 158b in each of configurations A, B, and C, The figures illustrate that, in this example, configuration B is most likely to achieve the highest possible current density, and therefore voltage potential, at modulation point 901. The field of configuration A may not extend deeply enough, and the field of configuration C may be too weak at that depth.

In some embodiments, modulation electrodes 158a, 158b may be spaced apart by about a distance of about 0.2 mm to 25 mm. In additional embodiments, modulation electrodes 158a, 158b may be spaced apart by a distance of about 1 mm to 10 mm, or between 4 mm and 7 mm. In other embodiments modulation electrodes 158a, 158b may be spaced apart by between approximately 6 mm and 7 mm.

Electrode configurations D, E, and F show that when modulation electrodes 158a, 158b of a constant distance are changed in size, the shape of the electric field facilitated by the electrodes changes. If a constant level of current is passed between when modulation electrodes 158a and 158b, the smaller electrodes of configuration D may facilitate a deeper field than that of configurations E and F, although the effect is less significant relative to changes in distance between the electrodes. As noted above, the facilitated electric fields are not of uniform strength throughout, and thus the voltage potential at seemingly similar locations within each of the electric fields of configurations D, E, and, F may vary considerably. Appropriate sizes of modulation electrodes 158a, 158b, may therefore depend on an implant location and a nerve to be stimulated.

In some embodiments, modulation electrodes 158a, 158b may have a surface area between approximately 0.01 $mm^2$ and 80 $mm^2$. In additional embodiments, modulation electrodes 158a, 158b may have a surface area between approximately 0.1 $mm^2$ and 4 $mm^2$. In other embodiments, modulation electrodes 158a, 158b may have a surface area of between approximately 0.25 $mm^2$ and 0.35 $mm^2$.

In some embodiments, modulation electrodes 158a, 158b may be arranged such that the electrodes are exposed on a single side of carrier 161. In such an embodiment, an electric field is generated only on the side of carrier 161 with exposed electrodes. Such a configuration may serve to reduce the amount of energy required to achieve neural modulation, because the entire electric field is generated on the same side of the carrier as the nerve, and little or no current is wasted traveling through tissue away from the nerve to be modulated. Such a configuration may also serve to make the modulation more selective. That is, by generating an electric field on the side of the carrier where there is a nerve to be modulated, nerves located in other areas of tissue (e.g. on the other side of the carrier from the nerve to be modulated), may avoid being accidentally modulated.

As discussed above, the utilization of electric fields having electrical field lines extending in a direction substantially parallel to the longitudinal direction of a nerve to be modulated may serve to lower the power requirements of modulation. This reduction in power requirements may permit the modulation of a nerve using less than 1.6 mA of current, less than 1.4 mA of current, less than 1.2 mA of current, less than 1 mA of current, less than 0.8 mA of current, less than 0.6 mA of current, less than 0.4 mA of current, and even less than 0.2 mA of current passed between modulation electrodes 158a, 158b.

Reducing the current flow required may have additional effects on the configuration of implant unit 110 and external unit 120. For example, the reduced current requirement may enable implant unit 110 to modulate a nerve without a requirement for a power storage unit, such as a battery or capacitor, to be implanted in conjunction with implant unit 110. For example, implant unit 110 may be capable of modulating a nerve using only the energy received via secondary antenna 152. Implant unit 110 may be configured to serve as a pass through that directs substantially all received energy to modulation electrodes 158a and 158b for nerve modulation. Substantially all received energy may refer to that portion of energy that is not dissipated or otherwise lost to the internal components of implant unit 110. Finally, the reduction in required current may also serve to reduce the amount of energy required by external unit 120. External unit 120 may be configured to operate successfully for an entire treatment session lasting from one to ten hours by utilizing a battery having a capacity of less than 240 mAh, less than 120 mAh, and even less than 60 mAh.

Whether a field inducing signal constitutes a modulation signal (resulting in an electric field that may cause nerve modulation) or a sub-modulation signal (resulting in an electric field not intended to cause nerve modulation) may ultimately be controlled by processor 144 of external unit 120. For example, in certain situations, processor 144 may determine that nerve modulation is appropriate. Under these conditions, processor 144 may cause signal source 144 and amplifier 146 to generate a modulation control signal on primary antenna 150 (i.e., a signal having a magnitude and/or duration selected such that a resulting secondary signal on secondary antenna 152 will provide a modulation signal at implant electrodes 158a and 158b).

Processor 144 may be configured to limit an amount of energy transferred from external unit 120 to implant unit 110. For example, in some embodiments, implant unit 110 may be associated with a threshold energy limit that may take into account multiple factors associated with the patient and/or the implant. For example, in some cases, certain nerves of a patient should receive no more than a predetermined maximum amount of energy to minimize the risk of damaging the nerves and/or surrounding tissue. Additionally, circuitry 180 of implant unit 110 may include components having a maximum operating voltage or power level that may contribute to a practical threshold energy limit of implant unit 110. For example, components including diodes may be included in implant unit 110 or in external unit 120 to limit power transferred from the external unit 120 to the implant unit 110. In some embodiments, diode 156 may function to limit the power level received by the patient. Processor 144 may be configured to account for such limitations when setting the magnitude and/or duration of a primary signal to be applied to primary antenna 150.

In addition to determining an upper limit of power that may be delivered to implant unit 110, processor 144 may also determine a lower power threshold based, at least in part, on an efficacy of the delivered power. The lower power threshold may be computed based on a minimum amount of power that enables nerve modulation (e.g., signals having power levels above the lower power threshold may constitute modulation signals while signals having power levels below the lower power threshold may constitute sub-modulation signals).

A lower power threshold may also be measured or provided in alternative ways. For example, appropriate circuitry or sensors in the implant unit 110 may measure a lower power threshold. A lower power threshold may be computed or sensed by an additional external device, and subsequently programmed into processor 144, or programmed into implant unit 110. Alternatively, implant unit 110 may be constructed with circuitry 180 specifically chosen to generate signals at the electrodes of at least the lower power threshold. In still another embodiment, an antenna of external unit 120 may be adjusted to accommodate or produce a signal corresponding to a specific lower power threshold. The lower power threshold may vary from patient to patient, and may take into account multiple factors, such as, for example, modulation characteristics of a particular patient's nerve fibers, a distance between implant unit 110 and external unit 120 after implantation, and the size and configuration of implant unit components (e.g., antenna and implant electrodes), etc.

Processor 144 may also be configured to cause application of sub-modulation control signals to primary antenna 150. Such sub-modulation control signals may include an amplitude and/or duration that result in a sub-modulation signal at electrodes 158a, 158b. While such sub-modulation control signals may not result in nerve modulation, such sub-modulation control signals may enable feedback-based control of the nerve modulation system. That is, in some embodiments, processor 144 may be configured to cause application of a sub-modulation control signal to primary antenna 150. This signal may induce a secondary signal on secondary antenna 152, which, in turn, induces a primary coupled signal component on primary antenna 150.

To analyze the primary coupled signal component induced on primary antenna 150, external unit 120 may include a feedback circuit 148 (e.g., a signal analyzer or detector, etc.), which may be placed in direct or indirect communication with primary antenna 150 and processor 144. Sub-modulation control signals may be applied to primary antenna 150 at any desired periodicity. In some embodiments, the sub-modulation control signals may be applied to primary antenna 150 at a rate of one every five seconds (or longer). In other embodiments, the sub-modulation control signals may be applied more frequently (e.g., once every two seconds, once per second, once per millisecond, once per nanosecond, or multiple times per second). Further, it should be noted that feedback may also be received upon application of modulation control signals to primary antenna 150 (i.e., those that result in nerve modulation), as such modulation control signals may also result in generation of a primary coupled signal component on primary antenna 150.

The primary coupled signal component may be fed to processor 144 by feedback circuit 148 and may be used as a basis for determining a degree of coupling between primary antenna 150 and secondary antenna 152. The degree of coupling may enable determination of the efficacy of the energy transfer between two antennas. Processor 144 may also use the determined degree of coupling in regulating delivery of power to implant unit 110.

Processor 144 may be configured with any suitable logic for determining how to regulate power transfer to implant unit 110 based on the determined degree of coupling. Processor 144 may, for example, utilize a baseline coupling range. Presumably, while the patient is awake, the tongue is not blocking the patient's airway and moves with the patient's breathing in a natural range, where coupling between primary antenna 150 and secondary antenna 152 may be within a baseline coupling range. A baseline coupling range may encompass a maximum coupling between primary antenna 150 and secondary antenna 152. A baseline coupling range may also encompass a range that does not include a maximum coupling level between primary antenna 150 and secondary antenna 152. Processor 144 may be configured to determine the baseline coupling range based on a command from a user, such as the press of a button on the patch or the press of a button on a suitable remote device. Alternatively or additionally, processor 144 may be configured to automatically determine the baseline coupling range when external unit 120 is placed such that primary antenna 150 and secondary antenna 152 are within range of each other. In such an embodiment, when processor 144 detects any degree of coupling between primary antenna 150 and secondary antenna 152, it may immediately begin tracking a baseline coupling range. Processor 144 may then determine a baseline coupling range when it detects that the only movement between primary antenna 150 and secondary antenna 152 is caused by a patient's natural breathing rhythm (i.e., the patient has secured the external unit to an appropriate location on their body). Additionally, processor 144 may be configured such that it measures coupling between the primary antenna 150 and the secondary antenna 152 for a specified period of time after activation in order to determine a baseline coupling range, such as 1 minute, 5 minutes, 10 minutes, etc.

Where the primary coupled signal component indicates that a degree of coupling has changed from a baseline coupling range, processor 144 may determine that secondary antenna 152 has moved with respect to primary antenna 150 (either in coaxial offset, lateral offset, or angular offset, or any combination). Such movement, for example, may be associated with a movement of the implant unit 110, and the tissue that it is associated with based on its implant location. Thus, in such situations, processor 144 may determine that modulation of a nerve in the patient's body is appropriate. More particularly, in response to an indication of a change in coupling, processor 144, in some embodiments, may cause application of a modulation control signal to primary antenna 150 in order to generate a modulation signal at implant electrodes 158a, 158b, e.g., to cause modulation of a nerve of the patient.

In an embodiment for the treatment of OSA, movement of an implant unit 110 may be associated with movement of the tongue, which may indicate the onset of a sleep apnea event or a sleep apnea precursor. The onset of a sleep apnea event of sleep apnea precursor may require the stimulation of the genioglossus muscle of the patient to relieve or avert the event. Such stimulation may result in contraction of the muscle and movement of the patient's tongue away from the patient's airway.

In embodiments for the treatment of head pain, including migraines, processor 144 may be configured to generate a modulation control signal based on a signal from a user, for example, or a detected level of neural activity in a sensory neuron (e.g. the greater occipital nerve or trigeminal nerve) associated with head pain. A modulation control signal generated by the processor and applied to the primary antenna 150 may generate a modulation signal at implant electrodes 158a, 158b, e.g., to cause inhibition or blocking (i.e. a down modulation) of a sensory nerve of the patient. Such inhibition or blocking may decrease or eliminate the sensation of pain for the patient.

In embodiments for the treatment of hypertension, processor 144 may be configured to generate a modulation control signal based on, for example, pre-programmed instructions and/or signals from an implant indicative of blood pressure. A modulation control signal generated by the processor and applied to the primary antenna 150 may generate a modulation signal at implant electrodes 158a, 158b, e.g., to cause either inhibition or stimulation of nerve of a patient, depending on the requirements. For example, a neuromodulator placed in a carotid artery or jugular vein (i.e. in the vicinity of a carotid baroreceptor), may receive a modulation control signal tailored to induce a stimulation signal at the electrodes, thereby causing the glossopharyngeal nerve associated with the carotid baroreceptors to fire at an increased rate in order to signal the brain to lower blood pressure. Similar modulation of the glossopharyngeal nerve may be achieved with a neuromodulator implanted in a subcutaneous location in a patient's neck or behind a patient's ear. A neuromodulator placed in a renal artery may receive a modulation control signal tailored to cause an inhibiting or blocking signal (i.e. a down modulation) at the electrodes, thereby inhibiting a signal to raise blood pressure carried from the renal nerves to the kidneys.

Modulation control signals may include stimulation control signals, and sub-modulation control signals may include sub-stimulation control signals. Stimulation control signals may have any amplitude, pulse duration, or frequency combination that results in a stimulation signal at electrodes 158a, 158b. In some embodiments (e.g., at a frequency of between about 6.5-13.6 MHz), stimulation control signals may include a pulse duration of greater than about 50 microseconds and/or an amplitude of approximately 0.5 amps, or between 0.1 amps and 1 amp, or between 0.05 amps and 3 amps. Sub-stimulation control signals may have a pulse duration less than about 500, or less than about 200 nanoseconds and/or an amplitude less than about 1 amp, 0.5 amps, 0.1 amps, 0.05 amps, or 0.01 amps. Of course, these values are meant to provide a general reference only, as various combinations of values higher than or lower than the exemplary guidelines provided may or may not result in nerve stimulation.

In some embodiments, stimulation control signals may include a pulse train, wherein each pulse includes a plurality of sub-pulses. An alternating current signal (e.g., at a frequency of between about 6.5-13.6 MHz) may be used to generate the pulse train, as follows. A sub-pulse may have a duration of between 50-250 microseconds, or a duration of between 1 microsecond and 2 milliseconds, during which an alternating current signal is turned on. For example, a 200 microsecond sub-pulse of a 10 MHz alternating current signal will include approximately 2000 periods. Each pulse may, in turn, have a duration of between 100 and 500 milliseconds, during which sub-pulses occur at a frequency of between 25 and 100 Hz. For example, a 200 millisecond pulse of 50 Hz sub-pulses will include approximately 10 sub-pulses. Finally, in a pulse train, each pulse may be separated from the next by a duration of between 0.2 and 2 seconds. For example, in a pulse train of 200 millisecond pulses, each separated by 1.3 seconds from the next, a new pulse will occur every 1.5 seconds. A pulse train of this embodiment may be utilized, for example, to provide ongoing stimulation during a treatment session. In the context of OSA, a treatment session may be a period of time during which a subject is asleep and in need of treatment to prevent OSA. Such a treatment session may last anywhere from about three to ten hours. In the context of other conditions to which neural modulators of the present disclosure are applied, a treatment session may be of varying length according to the duration of the treated condition.

Processor 144 may be configured to determine a degree of coupling between primary antenna 150 and secondary antenna 152 by monitoring one or more aspects of the primary coupled signal component received through feedback circuit 148. In some embodiments, processor 144 may determine a degree of coupling between primary antenna 150 and secondary antenna 152 by monitoring a voltage level associated with the primary coupled signal component, a current level, or any other attribute that may depend on the degree of coupling between primary antenna 150 and secondary antenna 152. For example, in response to periodic sub-modulation signals applied to primary antenna 150, processor 144 may determine a baseline voltage level or current level associated with the primary coupled signal component. This baseline voltage level, for example, may be associated with a range of movement of the patient's tongue when a sleep apnea event or its precursor is not occurring, e.g. during normal breathing. As the patient's tongue moves toward a position associated with a sleep apnea event, moves in a manner consistent with a precursor of sleep apnea, or moves in any other manner (e.g., vibration, etc.), the coaxial, lateral, or angular offset between primary antenna 150 and secondary antenna 152 may change. As a result, the degree of coupling between primary antenna 150 and secondary antenna 152 may change, and the voltage level or current level of the primary coupled signal component on primary antenna 150 may also change. Processor 144 may be configured to recognize a sleep apnea event or its precursor when a voltage level, current level, or other electrical characteristic associated with the primary coupled signal component changes by a predetermined amount or reaches a predetermined absolute value.

Figure 7:
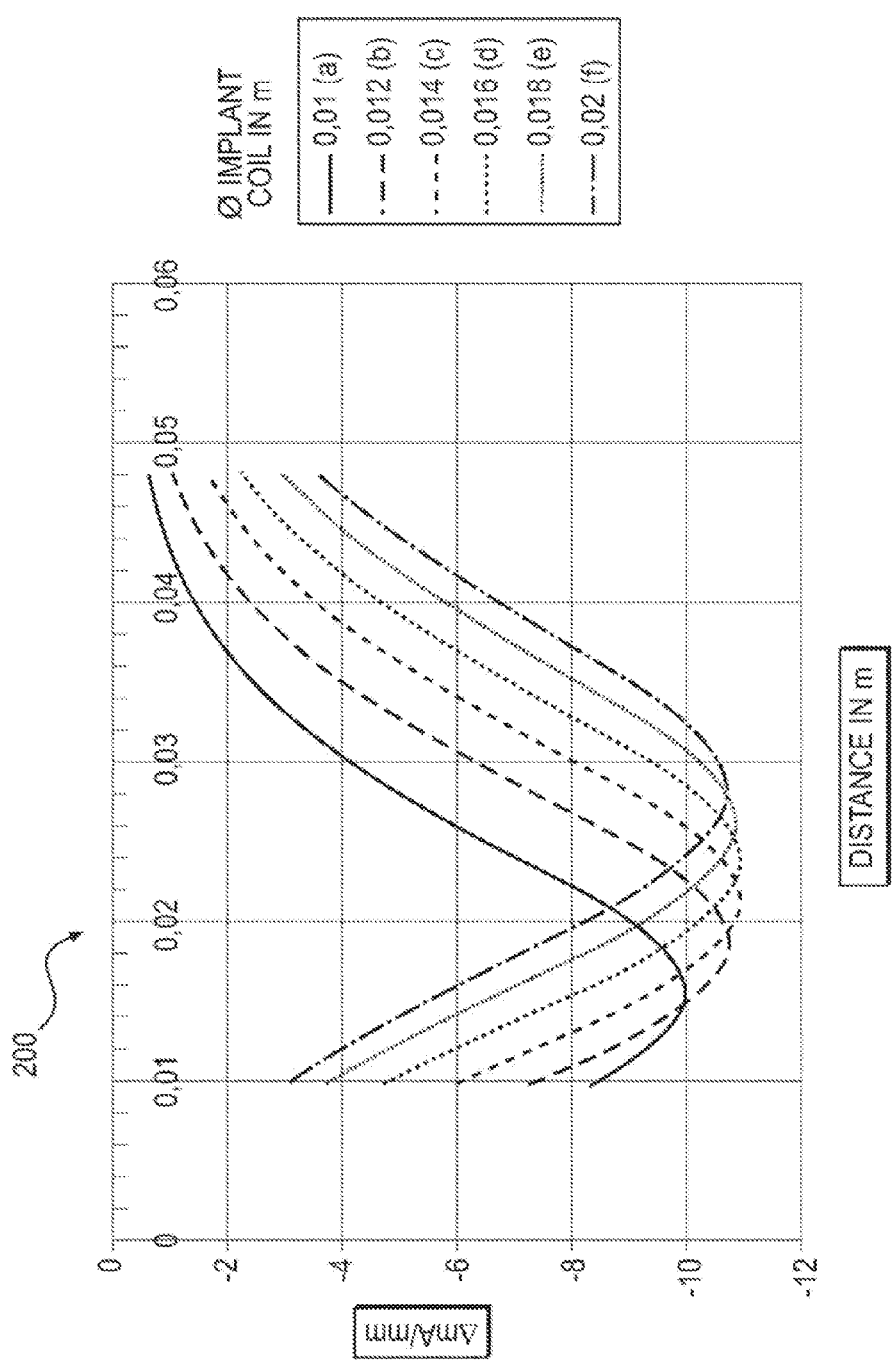
FIG. 7 illustrates a graph of quantities that may be used in determining energy delivery as a function coupling, according to an exemplary disclosed embodiment.

FIG. 7 provides a graph that illustrates this principle in more detail. For a two-coil system where one coil receives a radio frequency (RF) drive signal, graph 200 plots a rate of change in induced current in the receiving coil as a function of coaxial distance between the coils. For various coil diameters and initial displacements, graph 200 illustrates the sensitivity of the induced current to further displacement between the coils, moving them either closer together or further apart. It also indicates that, overall, the induced current in the secondary coil will decrease as the secondary coil is moved away from the primary, drive coil, i.e. the rate of change of induced current, in mA/mm, is consistently negative. The sensitivity of the induced current to further displacement between the coils varies with distance. For example, at a separation distance of 10 mm, the rate of change in current as a function of additional displacement in a 14 mm coil is approximately −6 mA/mm. If the displacement of the coils is approximately 22 mm, the rate of change in the induced current in response to additional displacement is approximately −11 mA/mm, which corresponds to a local maximum in the rate of change of the induced current. Increasing the separation distance beyond 22 mm continues to result in a decline in the induced current in the secondary coil, but the rate of change decreases. For example, at a separation distance of about 30 mm, the 14 mm coil experiences a rate of change in the induced current in response to additional displacement of about −8 mA/mm. With this type of information, processor 144 may be able to determine a particular degree of coupling between primary antenna 150 and secondary antenna 152, at any given time, by observing the magnitude and/or rate of change in the magnitude of the current associated with the primary coupled signal component on primary antenna 150.

Processor 144 may be configured to determine a degree of coupling between primary antenna 150 and secondary antenna 152 by monitoring other aspects of the primary coupled signal component. For example, in some embodiments, the non-linear behavior of circuitry 180 in implant unit 110 may be monitored to determine a degree of coupling. For example, the presence, absence, magnitude, reduction and/or onset of harmonic components in the primary coupled signal component on primary antenna 150 may reflect the behavior of circuitry 180 in response to various control signals (either sub-modulation or modulation control signals) and, therefore, may be used to determine a degree of coupling between primary antenna 150 and secondary antenna 152.

As shown in FIG. 6, circuitry 180 in implant unit 110 may constitute a non-linear circuit due, for example, to the presence of non-linear circuit components, such as diode 156. Such non-linear circuit components may induce non-linear voltage responses under certain operation conditions. Non-linear operation conditions may be induced when the voltage potential across diode 156 exceeds the activation threshold for diode 156. Thus, when implant circuitry 180 is excited at a particular frequency, this circuit may oscillate at multiple frequencies. Spectrum analysis of the secondary signal on secondary antenna 152, therefore, may reveal one or more oscillations, called harmonics, that appear at certain multiples of the excitation frequency. Through coupling of primary antenna 150 and secondary antenna 152, any harmonics produced by implant circuitry 180 and appearing on secondary antenna 152 may also appear in the primary coupled signal component present on primary antenna 150.

In certain embodiments, circuitry 180 may include additional circuit components that alter the characteristics of the harmonics generated in circuitry 180 above a certain transition point. Monitoring how these non-linear harmonics behave above and below the transition point may enable a determination of a degree of coupling between primary antenna 150 and secondary antenna 152. For example, as shown in FIG. 6, circuitry 180 may include a harmonics modifier circuit 154, which may include any electrical components that non-linearly alter the harmonics generated in circuitry 180. In some embodiments, harmonics modifier circuit 154 may include a pair of Zener diodes. Below a certain voltage level, these Zener diodes remain forward biased such that no current will flow through either diode. Above the breakdown voltage of the Zener diodes, however, these devices become conductive in the reversed biased direction and will allow current to flow through harmonics modifier circuit 154. Once the Zener diodes become conductive, they begin to affect the oscillatory behavior of circuitry 180, and, as a result, certain harmonic oscillation frequencies may be affected (e.g., reduced in magnitude).

Figure 8:
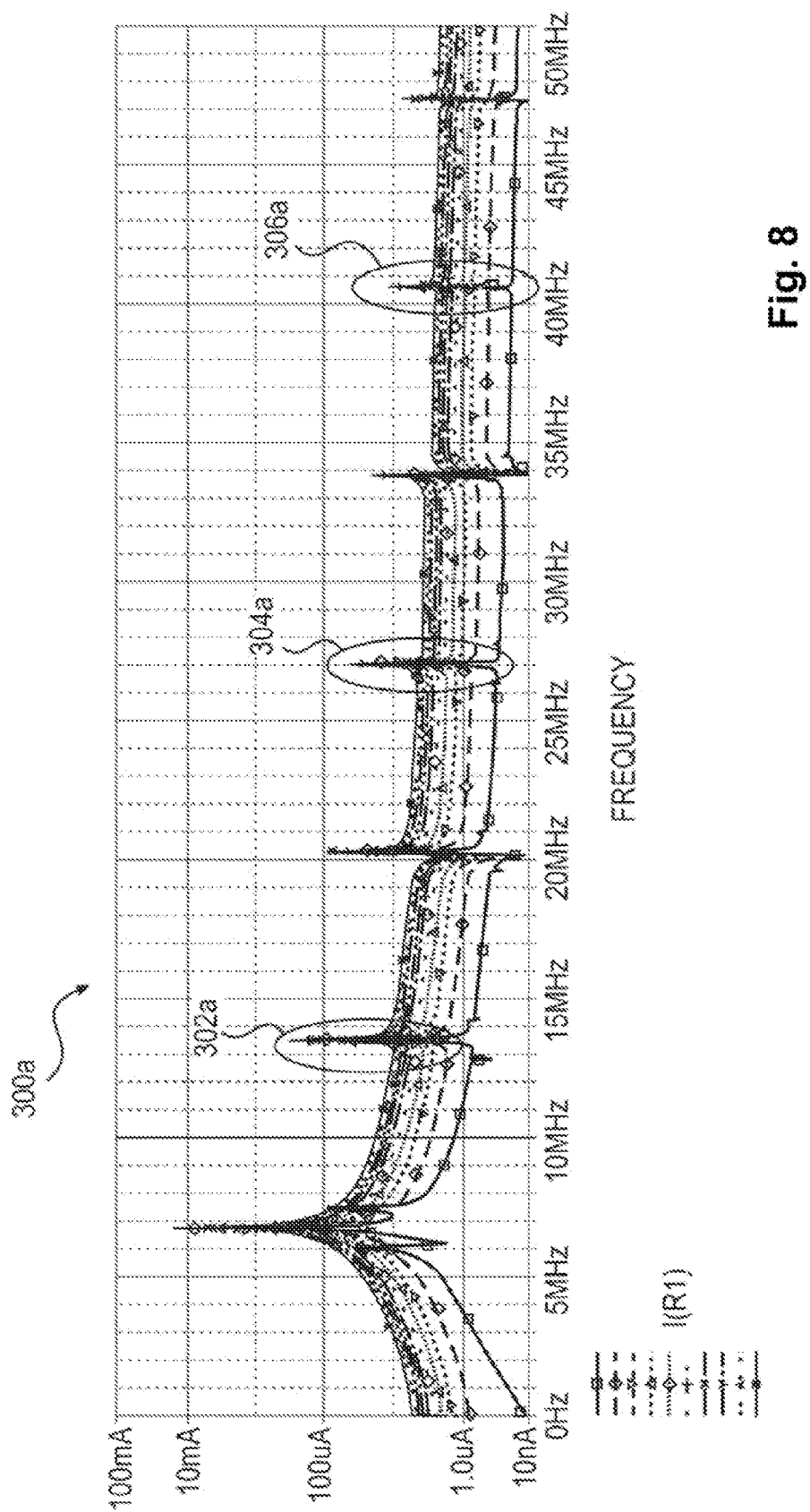
FIG. 8 depicts a graph illustrating non-linear harmonics.
Figure 9:
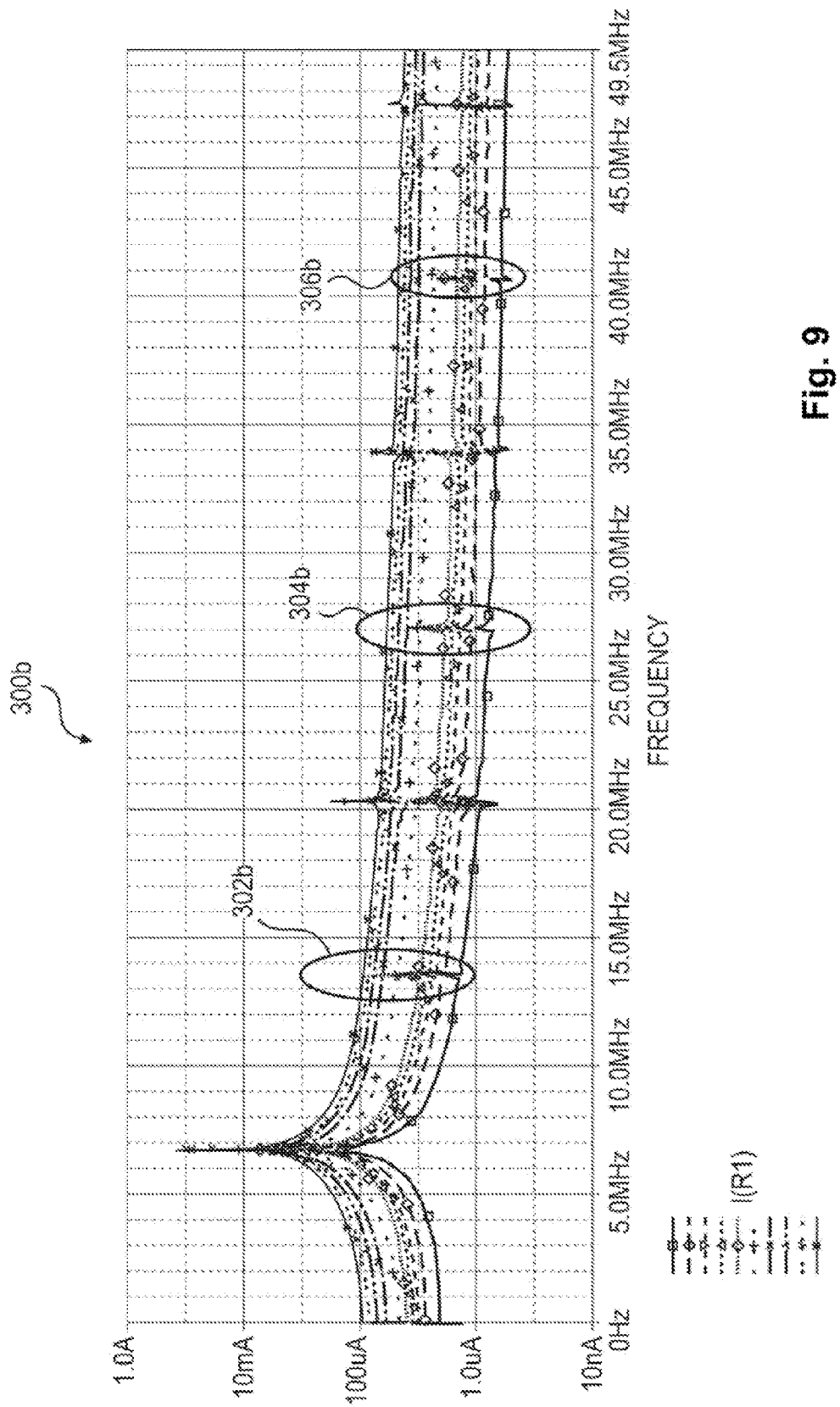
FIG. 9 depicts a graph of quantities that may be used in determining energy delivery as a function coupling, according to an exemplary disclosed embodiment.

FIGS. 8 and 9 illustrate this effect. For example, FIG. 8 illustrates a graph 300a that shows the oscillatory behavior of circuitry 180 at several amplitudes ranging from about 10 nanoamps to about 20 microamps. As shown, the primary excitation frequency occurs at about 6.7 MHz and harmonics appear both at even and odd multiples of the primary excitation frequency. For example, even multiples appear at twice the excitation frequency (peak 302a), four times the excitation frequency (peak 304a) and six times the excitation frequency (peak 306a). As the amplitude of the excitation signal rises between 10 nanoamps and 40 microamps, the amplitude of peaks 302a, 304a, and 306a all increase.

FIG. 9 illustrates the effect on the even harmonic response of circuitry 180 caused by harmonics modifier circuit 154. FIG. 9 illustrates a graph 300b that shows the oscillatory behavior of circuitry 180 at several amplitudes ranging from about 30 microamps to about 100 microamps. As in FIG. 8, FIG. 9 shows a primary excitation frequency at about 6.7 MHz and second, fourth, and sixth order harmonics (peaks 302b, 304b, and 306b, respectively) appearing at even multiples of the excitation frequency. As the amplitude of the excitation signal rises, however, between about 30 microamps to about 100 microamps, the amplitudes of peaks 302b, 304b, and 306b do not continuously increase. Rather, the amplitude of the second order harmonics decreases rapidly above a certain transition level (e.g., about 80 microamps in FIG. 8). This transition level corresponds to the level at which the Zener diodes become conductive in the reverse biased direction and begin to affect the oscillatory behavior of circuitry 180.

Monitoring the level at which this transition occurs may enable a determination of a degree of coupling between primary antenna 150 and secondary antenna 152. For example, in some embodiments, a patient may attach external unit 120 over an area of the skin under which implant unit 110 resides. Processor 144 can proceed to cause a series of sub-modulation control signals to be applied to primary antenna 150, which in turn cause secondary signals on secondary antenna 152. These sub-modulation control signals may progress over a sweep or scan of various signal amplitude levels. By monitoring the resulting primary coupled signal component on primary antenna 150 (generated through coupling with the secondary signal on secondary antenna 152), processor 144 can determine the amplitude of primary signal (whether a sub-modulation control signal or other signal) that results in a secondary signal of sufficient magnitude to activate harmonics modifier circuit 154. That is, processor 144 can monitor the amplitude of the second, fourth, or sixth order harmonics and determine the amplitude of the primary signal at which the amplitude of any of the even harmonics drops. FIGS. 8 and 9 illustrate the principles of detecting coupling through the measurement of non-linear harmonics. These Figures illustrate data based around a 6.7 MHz excitation frequency.

These principles, however, are not limited to the 6.7 MHz excitation frequency illustrated, and may be used with a primary signal of any suitable frequency.

In embodiments utilizing non-linear harmonics, the determined amplitude of the primary signal corresponding to the transition level of the Zener diodes (which may be referred to as a primary signal transition amplitude) may establish the baseline coupling range when the patient attaches external unit 120 to the skin. Thus, the initially determined primary signal transition amplitude may be fairly representative of a non-sleep apnea condition and may be used by processor 144 as a baseline in determining a degree of coupling between primary antenna 150 and secondary antenna 152. Optionally, processor 144 may also be configured to monitor the primary signal transition amplitude over a series of scans and select the minimum value as a baseline, as the minimum value may correspond to a condition of maximum coupling between primary antenna 150 and secondary antenna 152 during normal breathing conditions.

As the patient wears external unit 120, processor 144 may periodically scan over a range of primary signal amplitudes to determine a current value of the primary signal transition amplitude. In some embodiments, the range of amplitudes that processor 144 selects for the scan may be based on (e.g., near) the level of the baseline primary signal transition amplitude. If a periodic scan results in determination of a primary signal transition amplitude different from the baseline primary signal transition amplitude, processor 144 may determine that there has been a change from the baseline initial conditions. For example, in some embodiments, an increase in the primary signal transition amplitude over the baseline value may indicate that there has been a reduction in the degree of coupling between primary antenna 150 and secondary antenna 152 (e.g., because the implant has moved or an internal state of the implant has changed).

In addition to determining whether a change in the degree of coupling has occurred, processor 144 may also be configured to determine a specific degree of coupling based on an observed primary signal transition amplitude. For example, in some embodiments, processor 144 may have access to a lookup table or a memory storing data that correlates various primary signal transition amplitudes with distances (or any other quantity indicative of a degree of coupling) between primary antenna 150 and secondary antenna 152. In other embodiments, processor 144 may be configured to calculate a degree of coupling based on performance characteristics of known circuit components.

By periodically determining a degree of coupling value, processor 144 may be configured to determine, in situ, appropriate parameter values for the modulation control signal that will ultimately result in nerve modulation. For example, by determining the degree of coupling between primary antenna 150 and secondary antenna 152, processor 144 may be configured to select characteristics of the modulation control signal (e.g., amplitude, pulse duration, frequency, etc.) that may provide a modulation signal at electrodes 158a, 158b in proportion to or otherwise related to the determined degree of coupling. In some embodiments, processor 144 may access a lookup table or other data stored in a memory correlating modulation control signal parameter values with degree of coupling. In this way, processor 144 may adjust the applied modulation control signal in response to an observed degree of coupling.

Additionally or alternatively, processor 144 may be configured to determine the degree of coupling between primary antenna 150 and secondary antenna 152 during modulation. The tongue, or other structure on or near which the implant is located, and thus implant unit 110, may move as a result of modulation. Thus, the degree of coupling may change during modulation. Processor 144 may be configured to determine the degree of coupling as it changes during modulation, in order to dynamically adjust characteristics of the modulation control signal according to the changing degree of coupling. This adjustment may permit processor 144 to cause implant unit 110 to provide an appropriate modulation signal at electrodes 158a, 158b throughout a modulation event. For example, processor 144 may alter the primary signal in accordance with the changing degree of coupling in order to maintain a constant modulation signal, or to cause the modulation signal to be reduced in a controlled manner according to patient needs.

More particularly, the response of processor 144 may be correlated to the determined degree of coupling. In situations where processor 144 determines that the degree of coupling between primary antenna 150 and secondary antenna has fallen only slightly below a predetermined coupling threshold (e.g, during snoring or during a small vibration of the tongue or other sleep apnea event precursor), processor 144 may determine that only a small response is necessary. Thus, processor 144 may select modulation control signal parameters that will result in a relatively small response (e.g., a short stimulation of a nerve, small muscle contraction, etc.). Where, however, processor 144 determines that the degree of coupling has fallen substantially below the predetermined coupling threshold (e.g., where the tongue has moved enough to cause a sleep apnea event), processor 144 may determine that a larger response is required. As a result, processor 144 may select modulation control signal parameters that will result in a larger response. In some embodiments, only enough power may be transmitted to implant unit 110 to cause the desired level of response. In other words, processor 144 may be configured to cause a metered response based on the determined degree of coupling between primary antenna 150 and secondary antenna 152. As the determined degree of coupling decreases, processor 144 may cause transfer of power in increasing amounts. Such an approach may preserve battery life in the external unit 120, may protect circuitry 170 and circuitry 180, may increase effectiveness in addressing the type of detected condition (e.g., sleep apnea, snoring, tongue movement, etc.), and may be more comfortable for the patient.

In some embodiments, processor 144 may employ an iterative process in order to select modulation control signal parameters that result in a desired response level. For example, upon determining that a modulation control signal should be generated, processor 144 may cause generation of an initial modulation control signal based on a set of predetermined parameter values. If feedback from feedback circuit 148 indicates that a nerve has been modulated (e.g, if an increase in a degree of coupling is observed), then processor 144 may return to a monitoring mode by issuing sub-modulation control signals. If, on the other hand, the feedback suggests that the intended nerve modulation did not occur as a result of the intended modulation control signal or that modulation of the nerve occurred but only partially provided the desired result (e.g, movement of the tongue only partially away from the airway), processor 144 may change one or more parameter values associated with the modulation control signal (e.g., the amplitude, pulse duration, etc.).

Where no nerve modulation occurred, processor 144 may increase one or more parameters of the modulation control signal periodically until the feedback indicates that nerve modulation has occurred. Where nerve modulation occurred, but did not produce the desired result, processor 144 may re-evaluate the degree of coupling between primary antenna 150 and secondary antenna 152 and select new parameters for the modulation control signal targeted toward achieving a desired result. For example, where stimulation of a nerve causes the tongue to move only partially away from the patient's airway, additional stimulation may be desired. Because the tongue has moved away from the airway, however, implant unit 110 may be closer to external unit 120 and, therefore, the degree of coupling may have increased. As a result, to move the tongue a remaining distance to a desired location may require transfer to implant unit 110 of a smaller amount of power than what was supplied prior to the last stimulation-induced movement of the tongue. Thus, based on a newly determined degree of coupling, processor 144 can select new parameters for the stimulation control signal aimed at moving the tongue the remaining distance to the desired location.

In one mode of operation, processor 144 may be configured to sweep over a range of parameter values until nerve modulation is achieved. For example, in circumstances where an applied sub-modulation control signal results in feedback indicating that nerve modulation is appropriate, processor 144 may use the last applied sub-modulation control signal as a starting point for generation of the modulation control signal. The amplitude and/or pulse duration (or other parameters) associated with the signal applied to primary antenna 150 may be iteratively increased by predetermined amounts and at a predetermined rate until the feedback indicates that nerve modulation has occurred.

Processor 144 may be configured to determine or derive various physiologic data based on the determined degree of coupling between primary antenna 150 and secondary antenna 152. For example, in some embodiments the degree of coupling may indicate a distance between external unit 120 and implant unit 110, which processor 144 may use to determine a position of external unit 120 or a relative position of a patient's tongue. Monitoring the degree of coupling can also provide such physiologic data as whether a patient's tongue is moving or vibrating (e.g, whether the patient is snoring), by how much the tongue is moving or vibrating, the direction of motion of the tongue, the rate of motion of the tongue, etc.

In response to any of these determined physiologic data, processor 144 may regulate delivery of power to implant unit 110 based on the determined physiologic data. For example, processor 144 may select parameters for a particular modulation control signal or series of modulation control signals for addressing a specific condition relating to the determined physiologic data. If the physiologic data indicates that the tongue is vibrating, for example, processor 144 may determine that a sleep apnea event is likely to occur and may issue a response by delivering power to implant unit 110 in an amount selected to address the particular situation. If the tongue is in a position blocking the patient's airway (or partially blocking a patient's airway), but the physiologic data indicates that the tongue is moving away from the airway, processor 144 may opt to not deliver power and wait to determine if the tongue clears on its own. Alternatively, processor 144 may deliver a small amount of power to implant unit 110 (e.g., especially where a determined rate of movement indicates that the tongue is moving slowly away from the patient's airway) to encourage the tongue to continue moving away from the patient's airway or to speed its progression away from the airway. Additionally or alternatively, processor 144 may deliver power to implant unit 110 to initiate a tongue movement, monitor the movement of the tongue, and deliver additional power, for example, a reduced amount of power, if necessary to encourage the tongue to continue moving away from the patient's airway. The scenarios described are exemplary only. Processor 144 may be configured with software and/or logic enabling it to address a variety of different physiologic scenarios with particularity. In each case, processor 144 may be configured to use the physiologic data to determine an amount of power to be delivered to implant unit 110 in order to modulate nerves associated with the tongue with the appropriate amount of energy.

The disclosed embodiments may be used in conjunction with a method for regulating delivery of power to an implant unit. The method may include determining a degree of coupling between primary antenna 150 associated with external unit 120 and secondary antenna 152 associated with implant unit 110, implanted in the body of a patient. Determining the degree of coupling may be accomplished by processor 144 located external to implant unit 110 and that may be associated with external unit 120. Processor 144 may be configured to regulate delivery of power from the external unit to the implant unit based on the determined degree of coupling.

As previously discussed, the degree of coupling determination may enable the processor to further determine a location of the implant unit. The motion of the implant unit may correspond to motion of the body part where the implant unit may be attached. This may be considered physiologic data received by the processor. The processor may, accordingly, be configured to regulate delivery of power from the power source to the implant unit based on the physiologic data. In alternative embodiments, the degree of coupling determination may enable the processor to determine information pertaining to a condition of the implant unit. Such a condition may include location as well as information pertaining to an internal state of the implant unit. The processor may, according to the condition of the implant unit, be configured to regulate delivery of power from the power source to the implant unit based on the condition data.

In some embodiments, implant unit 110 may include at least one processor located on the implant. A processor located on implant unit 110 may perform all or some of the processes described with respect to the at least one processor associated with an external unit. For example, a processor associated with implant unit 110 may be configured to receive a control signal prompting the implant controller to turn on and cause a modulation signal to be applied to the implant electrodes for modulating a nerve. Such a processor may also be configured to monitor various sensors associated with the implant unit and to transmit this information back to and external unit. Power for the processor unit may be supplied by an onboard power source or received via transmissions from an external unit.

In other embodiments, implant unit 110 may be self-sufficient, including its own power source and a processor configured to operate the implant unit 110 with no external interaction. For example, with a suitable power source, the processor of implant unit 110 could be configured to monitor conditions in the body of a subject (via one or more sensors or other means), determining when those conditions warrant modulation of a nerve, and generate a signal to the electrodes to modulate a nerve. The power source could be regenerative based on movement or biological function; or the power sources could be periodically rechargeable from an external location, such as, for example, through induction.

In some embodiments, the at least one processor may be associated with the housing of external unit 120 and may be configured to communicate with a circuit implanted in the subject. The at least one processor may also be configured to receive a physiological signal from the subject via the implanted circuit. In response to the received physiological signal, the at least one processor may send a control signal, such as a closed loop control signal, to the implanted circuit. In some embodiments, the control signal may be predetermined to activate neuromuscular tissue within the tongue. Activating neuromuscular tissue may include, for example, causing muscular contractions and initiating a nerve action potential.

The physiological signal received from the implant unit may include any signal or signal component indicative of at least one physiological characteristic associated with the subject. In some embodiments, for example, the physiological characteristic may indicate whether a portion of the subject's body (e.g., the tongue) has moved, a direction of movement, a rate of change of movement, temperature, blood pressure, etc. The physiological signal may include any form of signal suitable for conveying information associated with at least some aspect of the subject. In some embodiments, the physiological signal may include an electromagnetic signal (e.g. microwave, infrared, radio-frequency (RF), etc.) having any desired waveform (e.g. sinusoidal, square wave, triangle wave, etc.). In some embodiments, the physiological signal may include any suitable amplitude or duration for transferring information about the subject.

In some embodiments, the physiological signal may include a primary coupled signal component on primary antenna 150. This primary coupled signal component may be induced on primary antenna 150 through coupling between primary antenna 150 of external unit 120 and secondary antenna 152 on implant unit 110.

In some embodiments, the physiological signal may include at least one aspect indicative of a movement of the subject's tongue. For example, movement of the tongue may cause relative motion between primary antenna 150 and secondary antenna 152, and this relative motion may result in variation of a degree of coupling between primary antenna 150 and secondary antenna 152. By monitoring the degree of coupling between primary antenna 150 and secondary antenna 152, for example, by monitoring signals or signal components present on primary antenna 150, relative motion between primary antenna 150 and secondary antenna 152 and, therefore, movement of the subject's tongue, may be detected.

As noted, in response to a received physiological signal, the at least one processor may cause a response based on the physiological signal. For example, in some embodiments, the at least one processor may be configured to cause the generation of a control signal (e.g. a closed loop control signal) intended to control at least one aspect of implant unit 110. The control signal may include a modulation control signal applied to primary antenna 150 such that a resulting secondary signal on secondary antenna 152 will provide a modulation signal at implant electrodes 158a and 158b.

In some embodiments, the processor may be configured to detect a sleep disordered breathing event based on the physiological signal and send the closed loop control signal in response to the detected sleep disordered breathing event. In some embodiments, the sleep disordered breathing event may be a precursor of sleep apnea, and the control signal may be predetermined to activate neuromuscular tissue within the tongue and may cause movement of the subject's tongue, for example, in a direction away from the posterior pharyngeal wall. The at least one processor may be further configured to determine a severity of the sleep disordered breathing event based on the physiological signal and vary a power level or duration of the control signal based on the determined severity of the sleep disordered breathing event. The severity of the event may be determined, for example, based on a determination of the relative movement between primary antenna 150 and secondary antenna 152 (e.g., an amplitude of movement, a rate of movement, a direction of movement, etc.). In some embodiments, a control signal may be sent if the relative movement exceeds a certain threshold.

A control signal may include any signal having suitable characteristics for causing a desired response in implant unit 110. For example, a control signal may have any suitable amplitude, duration, pulse width, duty cycle, or waveform (e.g. a sinusoidal signal, square wave, triangle wave, etc.) for causing a desired effect on implant unit 110 (e.g., modulation of nerve tissue in the vicinity of implant unit 110, etc.). A control signal may be generated and sent (e.g., to implant unit 110) within any desired response time relative to receipt of a physiological signal. In some embodiments, the response time may be set at 1 second, 500 milliseconds, 200 milliseconds, 100 milliseconds, 50 milliseconds, 20 milliseconds, 5 milliseconds, 1 millisecond, or any other time greater than 0 seconds and less than about 2 seconds. The control signal may be closed loop. As used herein, the term closed loop control signal may refer to any signal at least partially responsive to another signal, such as a control signal sent in response to a physiological signal. Or it may include any feedback response.

Based on the physiological signal, the processor may determine a quantity of energy to be sent via the closed loop control signal to implant unit 110. The amount of energy to be sent may be determined and/or varied based on any relevant factor including, for example, the time of day, a relevant biological factor of the subject (blood pressure, pulse, level of brain activity, etc.), the severity of the detected event, other characteristics associated with the detected event, or on any combination of factors. As noted, in embodiments where the physiological signal indicates a sleep disordered breathing event, the processor may be configured to determine a severity of the sleep disordered breathing event based on the physiological signal. In such embodiments, the processor may also determine an amount of energy to be provided to implant unit 110 as a response to the detected sleep disordered breathing event and in view of the determined severity of the event. The determined amount of energy may be transferred to implant unit 110 over any suitable time duration and at any suitable power level. In some embodiments, the power level and/or the duration of the control signal may be varied, and such variation may be dependent on the determined severity of the sleep disordered breathing event.

The power level and/or duration of the control signal may also be determined based on other factors. For example, the processor may vary a power level or duration associated with the control signal based on the efficiency of energy transfer between external unit 120 and implant unit 110. The processor may have access to such information through pre-programming, lookup tables, information stored in memory, etc. Additionally or alternatively, the processor may be configured to determine the efficiency of energy transfer, e.g., by monitoring the primary coupled signal component present on primary antenna 150, or by any other suitable method.

The processor may also vary the power level or duration of the control signal based on the efficacy of implant unit 110 (e.g., the implant unit's ability to produce a desired effect in response to the control signal). For example, the processor may determine that a certain implant unit 110 requires a certain amount of energy, a control signal of at least a certain power level and/or signal duration, etc., in order to produce a desired response (e.g., a modulation signal having an amplitude/magnitude of at least a desired level, etc.). Such a determination can be based on feedback received from implant unit 110 or may be determined based on lookup tables, information stored in memory, etc. In some embodiments, the power level or duration of the control signal may be determined based on a known or feedback-determined efficacy threshold (e.g., an upper threshold at or above which a desired response may be achieved) associated with implant unit 110.

Figure 10:
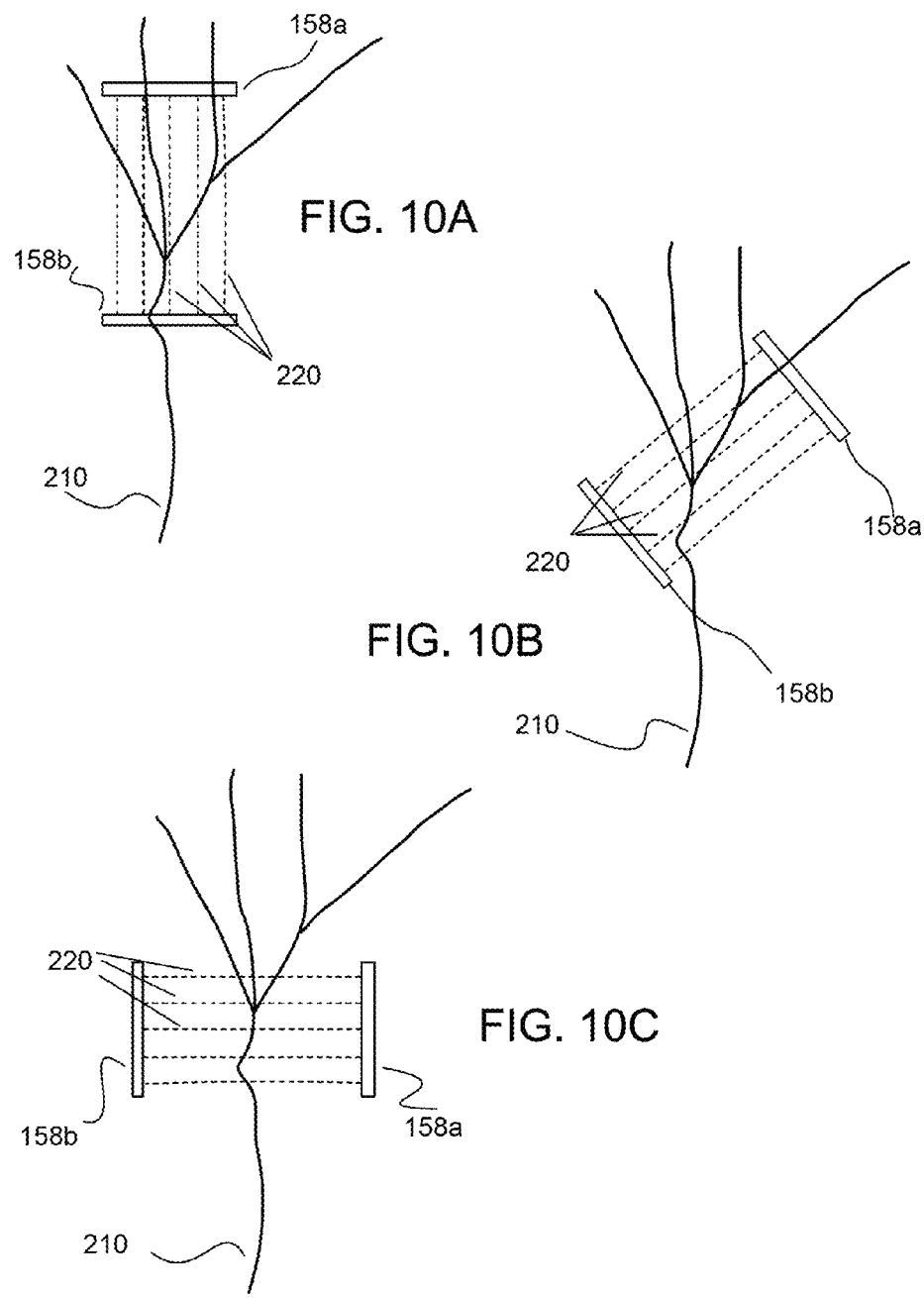
FIG. 10a illustrates a pair of electrodes spaced apart from one another along the longitudinal direction of nerve to facilitate generation of an electric field having field lines substantially parallel to the longitudinal direction of nerve.
FIG. 10b illustrates an embodiment wherein electrodes are spaced apart from one another in a longitudinal direction of at least a portion of nerve.
FIG. 10c illustrates a situation wherein electrodes are spaced apart from one another in a transverse direction of nerve.
Figure 14:
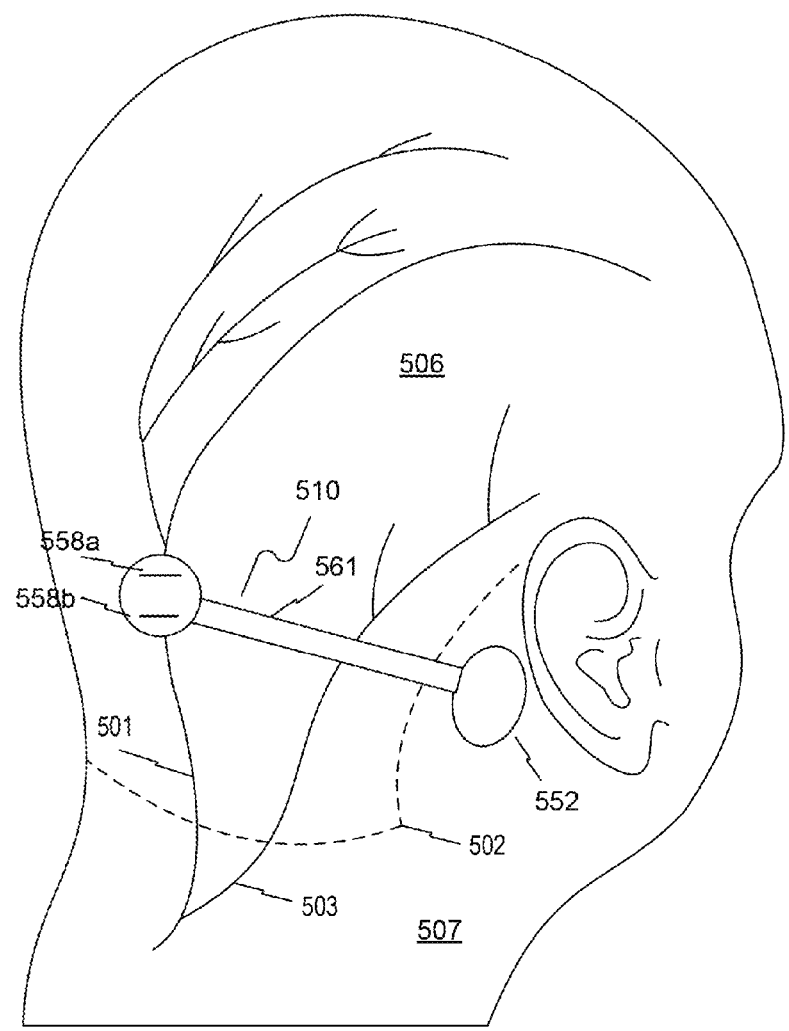
FIG. 14 depicts an exemplary implant location for the treatment of head pain.
Figure 15:
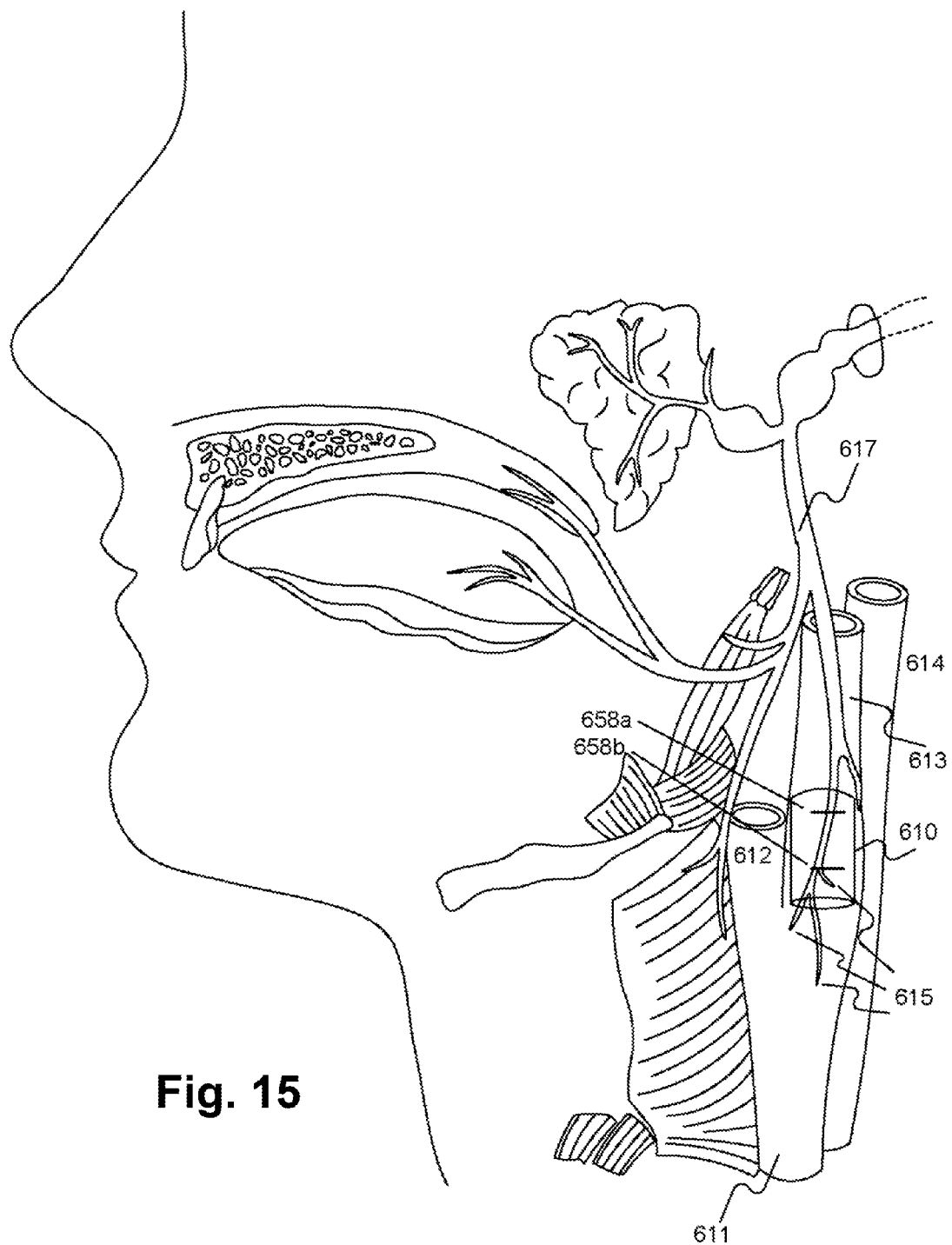
FIG. 15 depicts an exemplary implant location for the treatment of hypertension.
Figure 16:
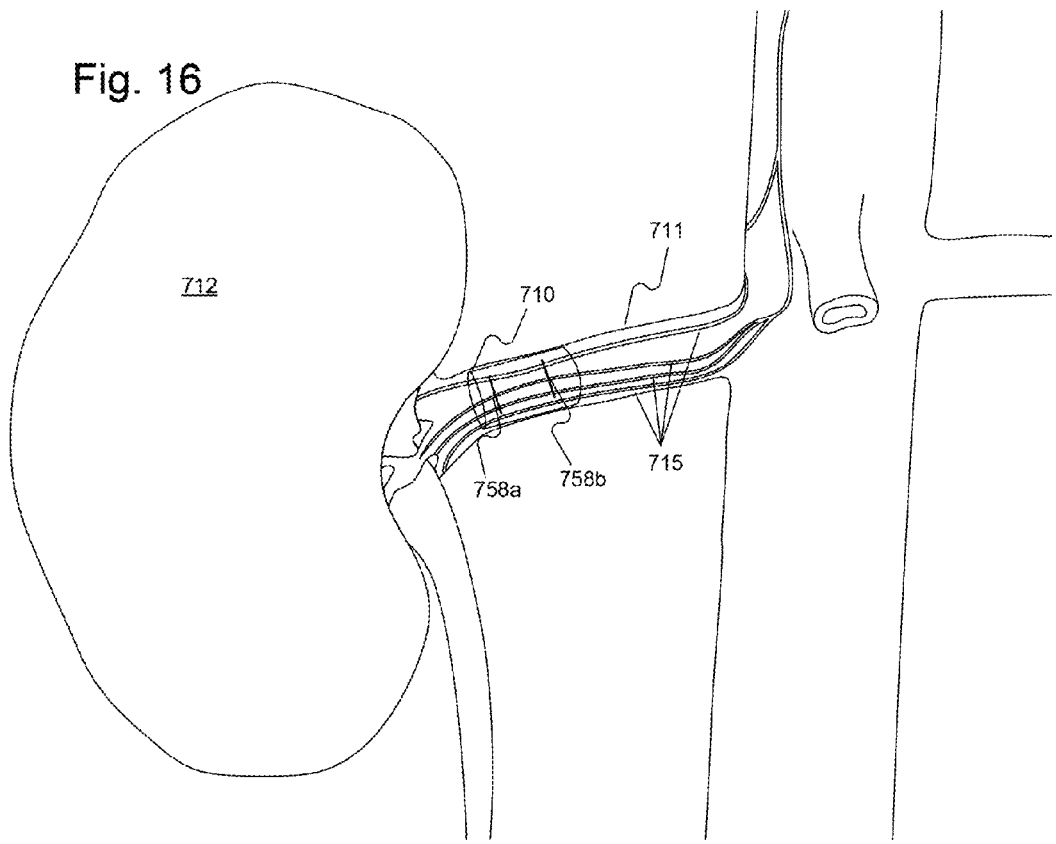
FIG. 16 depicts an exemplary implant location for the treatment of hypertension.

In some embodiments, implant unit 110 may be structurally configured to facilitate implantation in a location so as to increase the efficacy of modulation provided. For example, FIGS. 10 and 11 illustrate the anatomy of neck and tongue, and depict implantation locations suitable for neuromodulation treatment of OSA. FIG. 14 illustrates an exemplary implant unit 110 structurally configured for the treatment of head pain. FIGS. 15 and 16 illustrate exemplary implant units 110 structurally configured for the treatment of hypertension.

Figure 12:
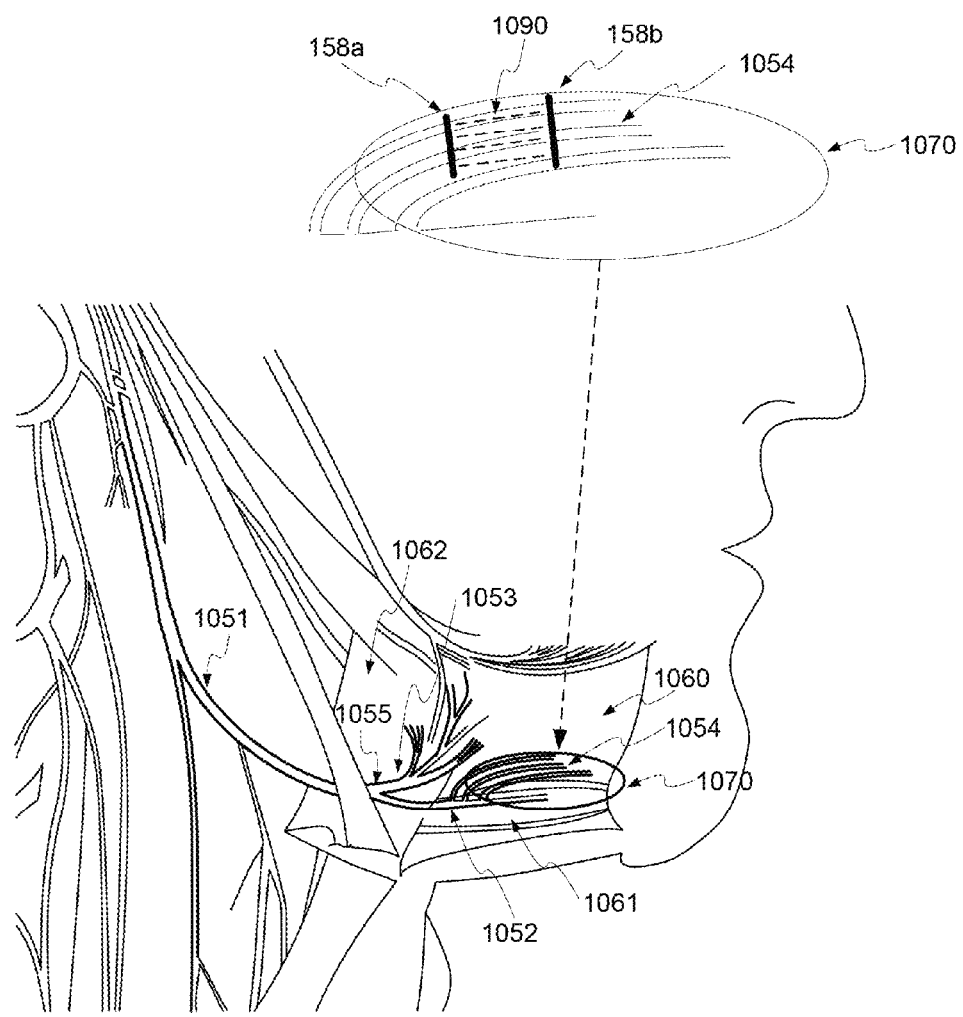
FIG. 12 depicts anatomy of the tongue and associated muscles and nerves.

FIG. 12 depicts an implantation location in the vicinity of a genioglossus muscle 1060 that may be accessed through derma on an underside of a subject's chin. FIG. 12 depicts hypoglossal nerve (i.e. cranial nerve XII). The hypoglossal nerve 1051, through its lateral branch 1053 and medial branch 1052, innervates the muscles of the tongue and other glossal muscles, including the genioglossus 1060, the hyoglossus 1062, mylohyoid (not shown) and the geniohyoid 1061 muscles. The mylohyoid muscle, not pictured in FIG. 12, forms the floor of the oral cavity, and wraps around the sides of the genioglossus muscle 1060. The horizontal compartment of the genioglossus 1060 is mainly innervated by the medial terminal fibers 1054 of the medial branch 1052, which diverges from the lateral branch 1053 at terminal bifurcation 1055. The distal portion of medial branch 1052 then variegates into the medial terminal fibers 1054. Contraction of the horizontal compartment of the genioglossus muscle 1060 may serve to open or maintain a subject's airway. Contraction of other glossal muscles may assist in other functions, such as swallowing, articulation, and opening or closing the airway. Because the hypoglossal nerve 1051 innervates several glossal muscles, it may be advantageous, for OSA treatment, to confine modulation of the hypoglossal nerve 1051 to the medial branch 1052 or even the medial terminal fibers 1054 of the hypoglossal nerve 1051. In this way, the genioglossus muscle, most responsible for tongue movement and airway maintenance, may be selectively targeted for contraction inducing neuromodulation. Alternatively, the horizontal compartment of the genioglossus muscle may be selectively targeted. The medial terminal fibers 1054 may, however, be difficult to affect with neuromodulation, as they are located within the fibers of the genioglossus muscle 1061. Embodiments of the present invention facilitate modulation the medial terminal fibers 1054, as discussed further below.

In some embodiments, implant unit 110, including at least one pair of modulation electrodes, e.g. electrodes 158a, 158b, and at least one circuit may be configured for implantation through derma (i.e. skin) on an underside of a subject's chin. When implanted through derma on an underside of a subject's chin, for example, into a sub-mandibular region, an implant unit 110 may be located proximate to medial terminal fibers 1054 of the medial branch 1052 of a subject's hypoglossal nerve 1051. An exemplary implant location 1070 is depicted in FIG. 12.

In some embodiments, implant unit 110 may be configured such that the electrodes 158a, 158b cause modulation of at least a portion of the subject's hypoglossal nerve through application of an electric field to a section of the hypoglossal nerve 1051 distal of a terminal bifurcation 1055 to lateral and medial branches 1053, 1052 of the hypoglossal nerve 1051. In additional or alternative embodiments, implant unit 110 may be located such that an electric field extending from the modulation electrodes 158a, 158b can modulate one or more of the medial terminal fibers 1054 of the medial branch 1052 of the hypoglossal nerve 1051. Thus, the medial branch 1053 or the medial terminal fibers 1054 may be modulated so as to cause a contraction of the genioglossus muscle 1060, which may be sufficient to either open or maintain a patient's airway. When implant unit 110 is located proximate to the medial terminal fibers 1054, the electric field may be configured so as to cause substantially no modulation of the lateral branch of the subject's hypoglossal nerve 1051. This may have the advantage of providing selective modulation targeting of the genioglossus muscle 1060.

As noted above, it may be difficult to modulate the medial terminal fibers 1054 of the hypoglossal nerve 1051 because of their location within the genioglossus muscle 1060. Implant unit 110 may be configured for location on a surface of the genioglossus muscle 1060. Electrodes 158a, 158b, of implant unit 110 may be configured to generate a parallel electric field 1090, sufficient to cause modulation of the medial terminal branches 1054 even when electrodes 158a, 158b are not in contact with the fibers of the nerve. That is, the anodes and the cathodes of the implant may be configured such that, when energized via a circuit associated with the implant 110 and electrodes 158a, 158b, the electric field 1090 extending between electrodes 158a, 158b may be in the form of a series of substantially parallel arcs extending through and into the muscle tissue on which the implant is located. A pair of parallel line electrodes or two series of circular electrodes may be suitable configurations for producing the appropriate parallel electric field lines. Thus, when suitably implanted, the electrodes of implant unit 110 may modulate a nerve in a contactless fashion, through the generation of parallel electric field lines.

Furthermore, the efficacy of modulation may be increased by an electrode configuration suitable for generating parallel electric field lines that run partially or substantially parallel to nerve fibers to be modulated. In some embodiments, the current induced by parallel electric field lines may have a greater modulation effect on a nerve fiber if the electric field lines 1090 and the nerve fibers to be modulated are partially or substantially parallel. The inset illustration of FIG. 12 depicts electrodes 158a and 158b generating electric field lines 1090 (shown as dashed lines) substantially parallel to medial terminal fibers 1054.

Figure 13:
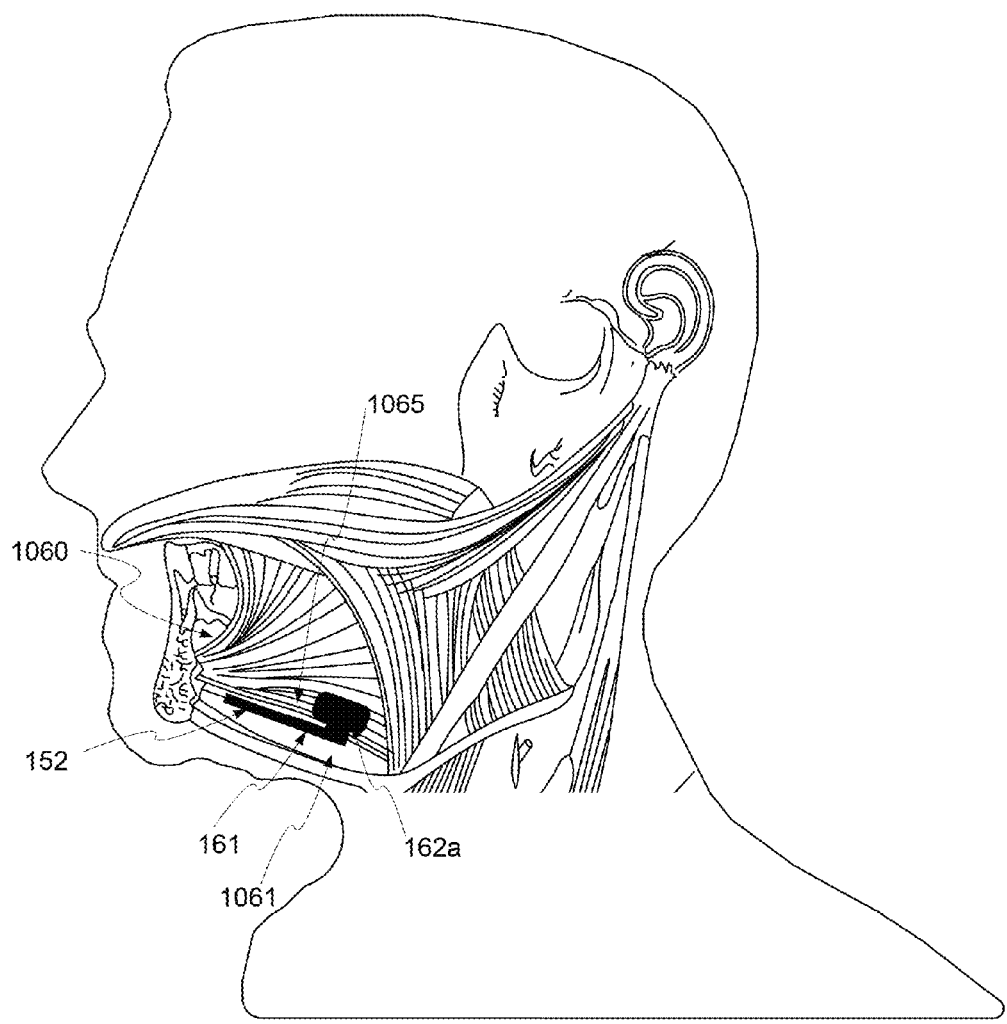
FIG. 13 depicts an exemplary implant location for the treatment of sleep apnea.

In order to facilitate the modulation of the medial terminal fibers 1054, implant unit 110 may be designed or configured to ensure the appropriate location of electrodes when implanted. An exemplary implantation is depicted in FIG. 13.

For example, a flexible carrier 161 of the implant may be configured such that at least a portion of a flexible carrier 161 of the implant is located at a position between the genioglossus muscle 1060 and the geniohyoid muscle 1061. Flexible carrier 161 may be further configured to permit at least one pair of electrodes arranged on flexible carrier 161 to lie between the genioglossus muscle 1060 and the mylohyoid muscle. Either or both of the extensions 162a and 162b of elongate arm 161 may be configured adapt to a contour of the genioglossus muscle. Either or both of the extensions 162a and 162b of elongate arm 161 may be configured to extend away from the underside of the subject's chin along a contour of the genioglossus muscle 1060. Either or both of extension arms 162a, 162b may be configured to wrap around the genioglossus muscle when an antenna 152 is located between the genioglossus muscle 1060 and geniohyoid muscle 1061. In such a configuration, antenna 152 may be located in a plane substantially parallel with a plane defined by the underside of a subject's chin, as shown in FIG. 13.

Flexible carrier 161 may be configured such that the at least one pair of spaced-apart electrodes can be located in a space between the subject's genioglossus muscle and an adjacent muscle. Flexible carrier 161 may be configured such that at least one pair of modulation electrodes 158a, 158b is configured for implantation adjacent to a horizontal compartment 1065 of the genioglossus muscle 1060. The horizontal compartment 1065 of the genioglossus 1060 is depicted in FIG. 13 and is the portion of the muscle in which the muscle fibers run in a substantially horizontal, rather than vertical, oblique, or transverse direction. At this location, the hypoglossal nerve fibers run between and in parallel to the genioglossus muscle fibers. In such a location, implant unit 110 may be configured such that the modulation electrodes generate an electric field substantially parallel to the direction of the muscle fibers, and thus, the medial terminal fibers 1054 of the hypoglossal nerve in the horizontal compartment.

FIG. 14 depicts an exemplary implant location for the treatment of head pain. As illustrated in FIG. 14, implant unit 510 includes an elongated carrier 561, secondary antenna 552, and modulation electrodes 558a, 558b. Implant unit 510 may also include any elements, such as circuitry, electrical components, materials, and any other features described previously with respect to implant unit 110. Implant 510 may be sized and configured such that it may be implanted with an end having secondary antenna 552 located beneath the skin in a substantially hairless region 507 of a subject. Elongated flexible carrier 561 may extend from this location, across a hairline 502 of the subject, to a location beneath the skin in a substantially haired region 506 of the subject in a vicinity of an occipital or other nerve that may be modulated to control or reduce head pain, such as a greater occipital nerve 501 or a lesser occipital nerve 503. As used herein, the term "substantially haired region" includes areas of a subject's head located on a side of the hairline where the scalp hair is located on a typical subject. Thus, a bald person may still have a "substantially haired region" on the side of the hairline on which hair typically grows. As used herein, the term "substantially hairless region" includes areas of a subject's head located on a side of the hairline where the scalp hair is not located on a typical subject. A "substantially hairless region," as used herein, is not required to be completely hairless, as almost all skin surfaces have some hair growth. As illustrated in FIG. 14, a substantially haired region 506 is separated from a substantially hairless region 507 by a hairline 502.

As described above, implant 510 may extend across the hairline 502 to a location in the vicinity of an occipital nerve. In FIG. 14, implant 510 extends across the hairline 502 to a location in the vicinity of greater occipital nerve 501. Furthermore, implant 510 may be configured for implantation such that electrodes 558a and 558b are spaced from each other along a longitudinal direction of an occipital nerve, such as the greater occipital nerve 501 shown in FIG. 14. Such a configuration permits electrodes 558a and 558b to facilitate an electrical field that extends in the longitudinal direction of the occipital nerve. In turn, the facilitated electrical field may be utilized to modulate greater occipital nerve 501, for example to block pain signals, as previously described.

The size and configuration of implant 510 illustrated in FIG. 14 may permit secondary antenna 552 to be located beneath the skin in a location where an external unit 520 (not illustrated), may be easily affixed to the skin, due to the lack of hair. External unit 520 may include any elements, such as circuitry, processors, batteries, antennas, electrical components, materials, and any other features described previously with respect to external unit 120. External unit 520 may be configured to communicate with implant 510 via secondary antenna 552 to deliver power and control signals, as described above with respect to external unit 120. Elongated carrier 561 may be flexible, and may permit modulation electrodes 558a and 558b to be located beneath the skin in a location suitable for modulating an occipital or other nerve for controlling head pain.

FIG. 15 depicts an exemplary implant location for the treatment of hypertension. As illustrated in FIG. 15, implant unit 610 may be configured for location or implantation inside a blood vessel. Such a configuration may include, for example, a flexible tubular carrier. Implant unit 610 may also include any elements, such as circuitry, electrical components, materials, and any other features described previously with respect to implant unit 110. Implant unit 610 may include modulation electrodes 658a, 658b configured to facilitate an electric field including field lines extending in the longitudinal direction of the blood vessel. For example, as illustrated in FIG. 15, implant unit 610 may be implanted in a carotid artery 611. Implant unit 610 may be located within carotid artery 611 in a location in the vicinity of carotid baroreceptors 615, at a location near the branching of the internal carotid artery 613 and the external carotid artery 612. As described previously, carotid baroreceptors 615 aid in the regulation of the blood pressure of a subject. Thus, implant unit 610, located within carotid artery 611 in the vicinity of carotid baroreceptors 615 may facilitate an electric field configured to modulate carotid baroreceptors 615, and, thus, affect the blood pressure of a subject. Affecting the blood pressure of a subject may include reducing, increasing, controlling, regulating, and influencing the blood pressure of a subject. The illustrated location is exemplary only, and implant unit 610 may be configured in alternate ways. For example, implant unit 610 may be configured for implantation in jugular vein 614 of the subject, in a location from which modulation of carotid baroreceptors 615 may be accomplished. Furthermore, implant unit 610 may be configured for implantation in a blood vessel, such as carotid artery 611 or jugular vein 614, in a location suitable for modulation of glossopharyngeal nerve 617. As described above, glossopharyngeal nerve 617 innervates carotid baroreceptors 615. Thus, glossopharyngeal nerve 617 may be directly modulated to affect blood pressure of a subject. Glossopharyngeal nerve 617 may also be modulated by an implant unit 610 located sub-cutaneously, in a non-intravascular location.

FIG. 16 depicts another exemplary implant location for the treatment of hypertension. As illustrated in FIG. 16, implant unit 710 may be configured for location or implantation inside a blood vessel. Such a configuration may include, for example, a flexible tubular carrier. Implant unit 710 may also include any elements, such as circuitry, electrical components, materials, and any other features described previously with respect to implant unit 110. Implant unit 710 may include modulation electrodes 758a, 758b configured to facilitate an electric field including field lines extending in the longitudinal direction of the blood vessel. For example, as illustrated in FIG. 15, implant unit 710 may be implanted in a renal artery 711. Implant unit 710 may be located within renal artery 711 in a location in the vicinity of renal nerves 715 surrounding renal artery 711 prior to its entry into kidney 712. As described previously, renal nerves 715 aid in the regulation of the blood pressure in humans. Thus, implant unit 710, located within renal artery 711 in the vicinity of renal nerves 715 may facilitate an electric field configured to modulate renal nerves 715, and, thus, affect the blood pressure of a subject. The illustrated location is exemplary only, and implant unit 710 may be configured in alternate ways suitable for the modulation of renal nerves 715.

Other embodiments of the present disclosure will be apparent to those skilled in the art from consideration of the specification and practice of the present disclosure.

While this disclosure provides examples of the neuromodulation devices employed for the treatment of certain conditions, usage of the disclosed neuromodulation devices is not limited to the disclosed examples. The disclosure of uses of embodiments of the invention for neuromodulation are to be considered exemplary only. In its broadest sense, the invention may be used in connection with the treatment of any physiological condition through neuromodulation. Alternative embodiments will become apparent to those skilled in the art to which the present invention pertains without departing from its spirit and scope. Accordingly, the scope of the present invention is defined by the appended claims rather than the foregoing description.

The invention claimed is:

1. A device, comprising:
   at least one pair of modulation electrodes configured for implantation in a sub-mandibular region and in a vicinity of a hypoglossal nerve to be modulated such that the electrodes are spaced apart from one another along a longitudinal direction of the hypoglossal nerve, the electrodes being further configured to facilitate an electric field in response to an applied electric signal, the electric field including field lines extending in the longitudinal direction of the hypoglossal nerve;
   a carrier sized and shaped for supporting the at least one pair of modulation electrodes in a manner permitting the at least one pair of electrodes to lie between a surface of a myelohyoid muscle and a surface of a genioglossus muscle, the carrier further including a portion configured to lie between a surface of a geniohyoid muscle and the surface of the genioglossus muscle; and
   at least one circuit, on the carrier, in electrical communication with the at least one pair of modulation electrodes and being configured to cause application of the electric signal applied at the at least one pair of modulation electrodes.

2. The device of claim 1, wherein the electrodes are configured to facilitate generation of the field lines extending in a direction substantially parallel to the longitudinal direction of at least a portion of the hypoglossal nerve.

3. The device of claim 1, wherein the carrier is made of a flexible material.

4. The device of claim 3, wherein the flexible material includes a biocompatible polymer including at least one of silicone, phenyltrimethoxysilane (PTMS), polymethyl methacrylate (PMMA), parylene C, polyimide, liquid polyimide, laminated polyimide, black epoxy, polyether ether ketone (PEEK), liquid crystal polymer (LCP), KAPTON, or combinations thereof.

5. The device of claim 1, wherein the at least one circuit and the at least one pair of modulation electrodes are supported by a common, flexible carrier.

6. The device of claim 1, wherein the at least one pair of modulation electrodes is supported by a flexible carrier configured to adapt to a contour of the surface of the genioglossus muscle to orient the at least one pair of modulation electrodes such that the electric field generated by the at least one pair of modulation electrodes includes field lines extending in a longitudinal direction of the hypoglossal nerve.

7. The device of claim 1, wherein the at least one pair of modulation electrodes includes line electrodes, point electrodes, or combinations thereof.

8. The device of claim 1, wherein each of the at least one pair of modulation electrodes includes an anode and a cathode spaced apart from one another by a distance of less than about 25 mm.

9. The device of claim 1, wherein each electrode of the at least one pair of modulation electrodes has a surface area of from about 0.01 mm$^2$ to about 80 mm$^2$.

10. The device of claim 1, wherein the at least one pair of modulation electrodes includes a first pair of electrodes provided on a first side of a flexible carrier and a second pair of electrodes provided on a second side of the flexible carrier different from the first side.

11. The device of claim 10, wherein the first pair of electrodes and the second pair of electrodes can be activated to simultaneously generate respective electric fields.

12. The device of claim 11, wherein the first pair of electrodes and the second pair of electrodes can be activated to sequentially generate respective electric fields.

13. The device of claim 1, wherein the at least one circuit is configured to receive an alternating current (AC) signal and cause application of at least one of a direct current (DC) signal and an AC signal to the at least one pair of modulation electrodes in response to the AC signal.

14. The device of claim 13, wherein the AC signal is received via an antenna associated with the at least one circuit.

15. A method of modulating a nerve, comprising:
   receiving an alternating current (AC) signal at a device configured to be implanted adjacent a hypoglossal nerve of a subject;
   generating a voltage signal in response to the AC signal;
   applying the voltage signal to the at least one pair of modulation electrodes configured for implantation in the vicinity of the hypoglossal nerve such that the electrodes are spaced apart from one another along a longitudinal direction of the hypoglossal nerve;
   generating an electrical field in response to the voltage signal applied to the at least one pair of modulation electrodes, the electric field including field lines extending in a longitudinal direction of the hypoglossal nerve; and
   modulating the hypoglossal nerve from a position spaced apart from the hypoglossal nerve.

16. The method of claim 15, wherein the electric field generated by the at least one pair of modulation electrodes includes field lines extending in a direction substantially parallel to a longitudinal direction of at least a portion of the hypoglossal nerve.

17. The method of claim 15, wherein the AC signal is received via an antenna electrically associated with the electrodes.

18. The method of claim 15, wherein each of the at least one pair of modulation electrodes includes an anode and a cathode spaced apart from one another by a distance of less than about 25 mm.

19. The method of claim 15, wherein each electrode of the at least one pair of modulation electrodes has a surface area of from about 0.01 mm$^2$ to about 80 mm$^2$.

* * * * *